US005849798A

United States Patent [19]
Charpentier et al.

[11] Patent Number: 5,849,798
[45] Date of Patent: Dec. 15, 1998

[54] POLYAROMATIC HETEROCYCLIC COMPOUNDS AND PHARMACEUTICAL/COSMETIC COMPOSITIONS COMPRISED THEREOF

[75] Inventors: Bruno Charpentier, Biot; Philippe Diaz, Nice; Philippe Nedoncelle, Grasse, all of France

[73] Assignee: Centre International De Recherches Dermatologiques Galderma, Valbonne, France

[21] Appl. No.: 615,843

[22] Filed: Mar. 14, 1996

[30] Foreign Application Priority Data

Mar. 14, 1995 [FR] France ................... 95 02926

[51] Int. Cl.$^6$ ............ A61K 31/35; A61K 31/40; C07D 311/04; C07D 311/76
[52] U.S. Cl. .......... 514/456; 514/233.5; 514/253; 514/320; 514/422; 514/432; 514/443; 544/151; 544/376; 546/196; 548/525; 549/23; 549/53; 549/58; 549/400; 549/403; 549/404; 549/405; 549/406
[58] Field of Search .................... 549/400, 403, 549/404, 405, 406, 23.53, 58; 548/525; 546/196; 544/151, 376; 514/233.5, 253, 320, 422, 456, 432, 443

[56] References Cited

U.S. PATENT DOCUMENTS

| | | | |
|---|---|---|---|
| 4,124,704 | 11/1978 | Scherrer | 424/180 |
| 4,234,577 | 11/1980 | Zilliken | 424/238 |
| 4,814,346 | 3/1989 | Albert et al. | 514/454 |

FOREIGN PATENT DOCUMENTS

| | | |
|---|---|---|
| 0025598 | 3/1981 | European Pat. Off. . |
| 0199636 | 10/1986 | European Pat. Off. . |
| 0267155 | 5/1988 | European Pat. Off. . |
| 0435322 | 7/1991 | European Pat. Off. . |
| 2006505 | 8/1971 | Germany . |
| 2164648 | 3/1986 | United Kingdom . |
| 92/21663 | 12/1992 | WIPO . |

OTHER PUBLICATIONS

Eur. J. Med. Chem., vol. 22, No. 2, 1987, pp. 119–123, C. Burali, et al, etc...
Chemical Abstracts, vol. 104, No. 12, Mar. 1986, Columbus, Ohio, USA; Abstracts No. 95475m, & JP-A-60 178 815 (Institute of Physical and Chemical Research) & Database Registry Chemical Abstracts Service, Columbus, Ohio, USA (STN), RN: 20879-05-4, 1985.
Chemical Abstracts, vol. 117, No. 15, Oct. 1992, Columbus, Ohio, USA; Abstract No. 142907j, & Antiviral Chem. Chemother, vol. 3, No. 4, 1992, pp. 195–202, N. Desideri, et al. & Database Registry Chemical Abstracts Service, Columbus, Ohio, U.S.A. (STN), RN: 143288-36-2; 143288-35-1; 143288-32-8; 143288-31-7.
Proc. Natl. Acad. Sci. U.S.A., vol. 90, No. 4, 1993, pp. 1247–1251, W.–M. Keung, et al, p. 1250, tableau 3, "equol".

Chemical Abstracts, vol. 110, No. 19, May 1989, Columbus, Ohio, USA; Abstract No. 172814z, & J. Med. Chem. vol. 32. No. 4, 1989, pp. 807–826, F.J. Brown, et al & Database Registry Chemical Abstracts Service, Columbus, Ohio, U.S.A. (STN), RN: 118683–55–9.
Chemical Abstracts, vol. 108, No. 19, May 1988, Columbus, Ohio, USA; Abstract No. 167116c, & CS-A-239 406 (M. Lacova, et al) & Database Registry Chemical Abstracts Service, Columbus, Ohio, U.S.A. (STN), RN: 113969–35–0; 113969–34–9, 1987.
Chemical Abstracts, vol. 110, No. 19, May 1989, Columbus, Ohio, USA; Abstract No. 172811w, & Acta Fac. Rerum Nat. Univ. Comenianae, Form. Prot. Nat., vol. 12, 1987, pp. 71–78, M. Lacova, et al & Database Registry Chemical Abstracts Service, Columbus, Ohio, U.S.A. (STN), RN: 118843–72–4; 84888–56–2.
Chemical Abstracts, vol. 119, No. 15, Oct. 1993, Columbus, Ohio, USA; Abstract No. 159959s, & New J. Chem., vol. 17, No. 3, 1993, pp. 211–224, P. Hapiot, et al & Database Registry Chemical Abstracts Service, Columbus, Ohio, U.S.A. (STN), RN: 150254–64–1.

(List continued on next page.)

*Primary Examiner*—Mukund J. Shah
*Assistant Examiner*—Brenda Coleman
*Attorney, Agent, or Firm*—Burns, Doane, Swecker & Mathis, L.L.P.

[57] ABSTRACT

Novel pharmaceutically/cosmetically-active polyaromatic heterocyclic compounds have the structural formula (I):

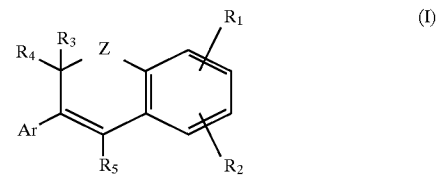

in which Z is a divalent radical selected from among —O—, —S— or —Nr'— and Ar is either a radical having the following structural formula (II):

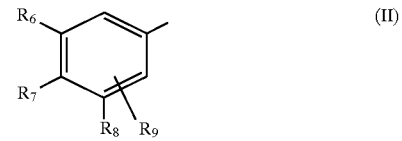

or a radical having the following structural formula (III):

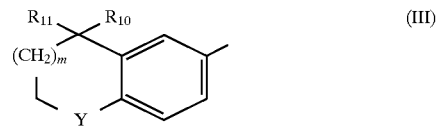

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

37 Claims, 2 Drawing Sheets

OTHER PUBLICATIONS

Chemical Abstracts, vol. 54, No. 9, May 1960, Columbus, Ohio, USA; Abstract No. 8883g, & Bull. Soc. Chim. France, 1959, pp. 521–529, R. Royer, et al.

Chemical Abstracts, vol. 57, No. 8, Oct. 1962, Columbus, Ohio, USA; Abstract No. 9773h, & Bull. Soc. Chim. France, 1959, pp. 1468–1473, R. Royer, et al.

Major et al., Synthese der naturlichen Isoflav–3–ene Haginin A, B, and D, Liebigs Ann. Chem., No. 6, pp. 555–558, 1988.

Ramakanth et al., A Novel Photochemical Ring Contraction Of 11 a–Methylpterocarpans, Tetrahedron, vol. 42, No. 3, pp. 863–876, 1988.

Miyase et al., Studies on the Constituents of *Lespedeza cyrtobotrya* Miq. II. The Structures of Haginin C, Haginin D and Lespedeol C, Chem. Pharm. Bull., vol. 29, No. 8, pp. 2205–2209, 1981.

POLYAROMATIC HETEROCYCLIC COMPOUNDS AND PHARMACEUTICAL/COSMETIC COMPOSITIONS COMPRISED THEREOF

BACKGROUND OF THE INVENTION

1. Technical Field of the Invention

The present invention relates to novel polyaromatic heterocyclic compounds and to pharmaceutical/cosmetic compositions comprised thereof; the subject compounds are especially useful in human or veterinary medicine, or alternatively in cosmetic compositions.

This invention also relates to unique intermediates for the synthesis of the subject novel polyaromatic heterocyclic compounds.

SUMMARY OF THE INVENTION

The compounds according to the invention display marked activity in the fields of cell differentiation and proliferation, and are particularly useful in the topical and systemic treatment of dermatological conditions associated with a keratinization disorder, dermatological conditions (and the like) including an inflammatory and/or immunoallergic component, and dermal or epidermal proliferations, whether benign or malignant. The subject compounds can, in addition, be used for the treatment of degeneration diseases of the connective tissue, for combating skin aging, whether photoinduced or chronologic, and for treating cicatrization disorders. They are also useful for ophthalmological applications, especially for the treatment of corneopathies.

Too, the compounds according to the invention can be formulated into cosmetic compositions for body and hair care.

Briefly, the polyaromatic heterocyclic compounds according to the invention have the following structural formula (I):

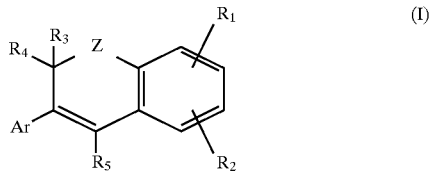

in which Z is a divalent radical selected from among —O—, —S— or —Nr'—; Ar is either a radical having the following structural formula (II):

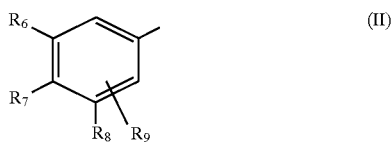

or a radical having the following structural formula (III):

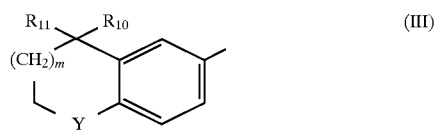

wherein m is equal to 0 or 1; $R_1$ is (i) a hydrogen atom, (ii) the —$CH_3$ radical, (iii) a radical —$(CH_2)_p$—O—$R_{12}$, (iv) a radical —$OR_{12}$, (v) a radical:

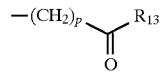

or (vi) a radical —$S(O)_tR_{14}$, wherein $R_{12}$, $R_{13}$, $R_{14}$, p and t are as defined below; $R_2$ is a hydrogen atom, a halogen atom, a lower alkyl radical or a radical —$OR_{12}$, wherein $R_{12}$ is as defined below; $R_3$ and $R_4$, which may be identical or different, are each a halogen atom, a hydrogen atom, a lower alkyl radical or a radical $OR_{12}$, wherein $R_{12}$ is as defined below; $R_5$ is a halogen atom, a hydrogen atom, a lower alkyl radical or a radical —$OR_{15}$, wherein $R_{15}$ is as defined below; $R_6$, $R_7$, $R_8$ and $R_9$, which may be identical or different, are each a hydrogen atom, a halogen atom, an alkyl radical, a cycloalkyl radical, a radical —$(Z_1)_n$—$(CH_2)_q$—CO—$R_{13}$, or a radical —$Z_2$—$R_{12}$, with the proviso that at least two of the radicals $R_6$, $R_7$, $R_8$ and $R_9$ are other than a hydrogen atom and further wherein $Z_1$, $Z_2$, $R_{12}$, $R_{13}$, n and q are as defined below; $R_{10}$ and $R_{11}$ are lower alkyl radicals; Y is a divalent radical selected from among —C($R_{11}$)$_2$—, —O—, —S—, —Nr'—, —CH(OH)—, —CO—, —SO— and —$SO_2$—, wherein $R_{11}$ is as defined above and r' is as defined below, with the proviso that $R_1$, $R_2$, $R_3$, $R_4$ and $R_5$ cannot simultaneously each be a hydrogen atom; $R_{12}$ is a hydrogen atom, a lower alkyl radical, an aryl radical, an aralkyl radical, a polyhydroxyalkyl radical, a polyether radical or a lower acyl radical; $R_{13}$ is (a) a hydrogen atom, (b) a radical:

wherein r and r' are as defined below, or (c) a radical —$OR_{14}$, wherein $R_{14}$ is as defined below; $R_{14}$ is a hydrogen atom, an alkyl radical, a mono- or polyhydroxyalkyl radical, an optionally substituted aryl or aralkyl radical, or a sugar or amino acid residue; $R_{15}$ is a hydrogen atom, a lower alkyl radical, an aryl radical, an aralkyl radical or a polyether radical; r and r', which may be identical or different, are each a hydrogen atom, a lower alkyl radical, an optionally substituted aryl radical, or an amino acid or sugar residue, with the proviso that r and r' may together form, with the nitrogen atom from which they depend, a heterocycle; $Z_1$ is O, S or Nr'; $Z_2$ is O or S, n is equal to 0 or 1; p is equal to 0, 1, 2 or 3; g is an integer ranging from 0 to 10; t is equal to 0, 1, 2 or 3; and the optical and geometric isomers and salts thereof.

When the compounds according to the invention are in the form of salts, by addition of a base thereto, these are preferably salts of an alkali or alkaline earth metal, or, alternatively, of zinc or of an organic amine.

When the subject compounds are in the form of salts, by addition of an acid thereto, these are pharmaceutically or cosmetically acceptable salts prepared by addition of an inorganic or organic acid thereto, in particular hydrochloric acid, sulfuric acid, acetic acid, citric acid, fumaric acid, hemisuccinic acid, maleic acid and mandelic acid.

Preferably, $R_1$ and $R_2$ are not simultaneously either a hydrogen atom or a hydrogen atom and a halogen atom, respectively.

BRIEF DESCRIPTION OF THE DRAWINGS

The FIGURES OF DRAWING set forth reaction schemes/mechanisms illustrating syntheses for the preparation of the polyaromatic heterocyclic compounds according to the present invention.

DETAILED DESCRIPTION OF BEST MODE AND PREFERRED EMBODIMENTS OF THE INVENTION

Figure 1:
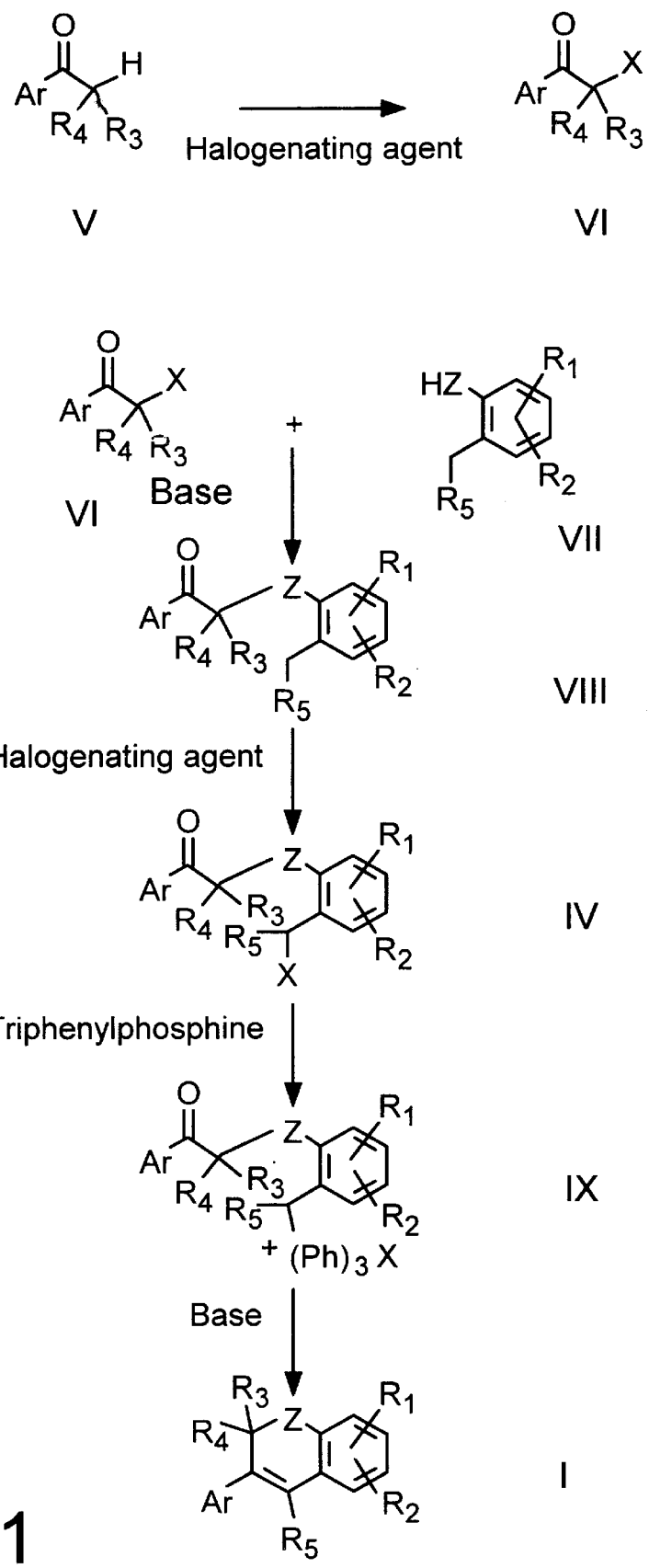

More particularly according to the present invention, by "lower alkyl radical" is intended an alkyl radical having from 1 to 6 carbon atoms and preferably the methyl, ethyl, isopropyl, butyl, tert-butyl and hexyl radicals.

By "lower acyl radical" is intended a radical having from 1 to 6 carbon atoms and preferably the acetyl, propionyl and pivaloyl radicals.

By "protecting group for the amine function" are intended the corresponding groups described in *Protecting Groups in Organic Synthesis* by T. W Greene, Ed. by John Wiley and Sons (1981).

By "cycloalkyl radical" is intended a cyclic or polycyclic alkane radical having from 1 to 10 carbon atoms, optionally substituted by one or more halogen atoms or one or more hydroxyl groups and preferably adamantyl or 1-methylcyclohexyl radicals.

By "polyether radical" is intended a radical having from 1 to 6 carbon atoms and from 1 to 3 oxygen or sulfur atoms, such as the methoxymethyl ether, methoxyethoxymethyl ether or methylthiomethyl ether radicals.

By "monohydroxyalkyl radical" is intended a radical preferably having 2 or 3 carbon atoms, in particular a 2-hydroxyethyl, 2-hydroxypropyl or 3-hydroxypropyl radical.

By "polyhydroxyalkyl radical" is intended a radical having from 1 to 6 carbon atoms and from 1 to 5 hydroxyl groups, such as the 2,3-dihydroxypropyl, 2,3,4-trihydroxybutyl and 2,3,4,5-tetrahydroxypentyl radicals, or a pentaerythritol residue.

By "optionally substituted aryl radical" is preferably intended a phenyl radical optionally substituted by one or more halogen atoms, or by at least one hydroxyl, nitro or methoxy group.

By "optionally substituted aralkyl radicals" is preferably intended the benzyl or phenethyl radical, optionally substituted by one or more halogen atoms, or by at least one hydroxyl, nitro or methoxy group.

By "amino acid residue" is intended a residue derived, in particular, from one of the 20 amino acids of L or D configuration which constitute mammalian proteins. Residues derived from lysine, glycine or aspartic acid are the preferred.

By "sugar residue" is intended a residue derived, in particular, from glucose, galactose, mannose or glucuronic acid.

Lastly, by "heterocycle" is preferably intended a piperidino, morpholino, pyrrolidino or piperazino radical, optionally substituted at the 4-position by a $C_1$–$C_6$ alkyl radical or a mono- or polyhydroxyalkyl radical as defined above.

Among the compounds of formula (I) according to the present invention, particularly representative are the following:

3-[(3-(1-Adamantyl)-4-methoxyphenyl)-2H-1-benzopyran]-7-carboxylic acid;

Methyl 3-[(3-(1-adamantyl)-4-methoxyphenyl)-2H-1-benzopyran]-7-carboxylate;

Methyl 3-[(3-(1-adamantyl)-4-hydroxyphenyl)-2H-1-benzopyran]-7-carboxylate;

3-[(3-(1-Adamantyl)-4-hydroxyphenyl)-2H-1-benzopyran]-7-carboxylic acid;

3-[(3-(1-Adamantyl)-4-methoxyphenyl)-2H-1-benzopyran]-6-carboxylic acid;

Methyl 3-[(3-(1-adamantyl)-4-methoxyphenyl)-2H-1-benzopyran]-6-carboxylate;

3-[(3-(1-Adamantyl)-4-hydroxyphenyl)-2H-1-benzopyran]-6-carboxylic acid;

3-[(5,6,7,8-Tetrahydro-5,5,8,8-tetramethyl-2-naphthyl)-2H-1-benzopyran]-7-carboxylic acid;

Methyl 3-[(5,6,7,8-tetrahydro-5,5,8,8-tetramethyl-2-naphthyl)-2H-1-benzopyran]-7-carboxylate;

3-[(5,6,7,8-Tetrahydro-5,5,8,8-tetramethyl-2-naphthyl)-2H-1-benzopyran]-6-carboxylic acid;

Methyl 3-[(5,6,7,8-tetrahydro-5,5,8,8-tetramethyl-2-naphthyl)-2H-1-benzopyran]-6-carboxylate;

Methyl 3-[(3,5-di-tert-butyl-4-hydroxyphenyl)-2H-1-benzopyran]-6-carboxylate;

3-[(3,5-Di-tert-butyl-4-methoxyphenyl)-2H-1-benzopyran]-6-carboxylic acid;

3-[(3,5-Di-tert-butyl-4-hydroxyphenyl)-2H-1-benzopyran]-6-carboxylic acid;

Methyl 3-[(3,5-di-tert-butyl-4-methoxyphenyl)-2H-1-benzopyran]-7-carboxylate;

Methyl 3-[($^3$,$^5$-di-tert-butyl-4-methoxyphenyl)-2H-1-benzopyran]-6-carboxylate;

3-[(3,5-Di-tert-butyl-4-hydroxyphenyl)-2H-1-benzopyran]-7-carboxylic acid;

3-[(3,5-Di-tert-butyl-4-methoxyphenyl)-2H-1-benzopyran]-7-carboxylic acid;

Methyl 3-[(4-(1-adamantyl)-3-methoxyphenyl)-2H-1-benzopyran]-6-carboxylate;

3-[(4-(1-Adamantyl)-3-methoxyphenyl)-2H-1-benzopyran]-6-carboxylic acid;

Methyl 3-[(3-tert-butyl-4-hydroxyphenyl)-2H-1-benzopyran]-7-carboxylate;

3-[(3-tert-Butyl-4-hydroxyphenyl)-2H-1-benzopyran]-7-carboxylic acid;

Methyl 3-[(3-(1-adamantyl)-4-methoxyethoxymethoxyphenyl)-2H-1-benzopyran]-7-carboxylate;

3-[(3-(1-Adamantyl)-4-methoxyethoxymethoxyphenyl)-2H-1-benzopyran]-7-carboxylic acid;

3-[(5,6,7,8-Tetrahydro-5,5,8,8-tetramethyl-2-naphthyl)-2H-1-benzopyran]-7-methyl alcohol;

3-[(5,6,7,8-Tetrahydro-5,5,8,8-tetramethyl-2-naphthyl)-2H-1-benzopyran]-7-carboxaldehyde;

3-[(3,5-Di-tert-butyl-4-hydroxyphenyl)-2H-1-benzopyran]-7-carboxanilide;

3-[(5,6,7,8-Tetrahydro-5,5,8,8-tetramethyl-2-naphthyl)-2H-1-benzopyran]-7-carboxylic acid morpholide;

$^3$-[(5,6,7,8-Tetrahydro-5,5,8,8-tetramethyl-2-naphthyl)-2H-1-benzopyran]-7-glyoxylic acid morpholide;

N-Butyl-3-[(5,6,7,8-tetrahydro-5,5,8,8-tetramethyl-2-naphthyl)-2H-1-benzopyran]-7-carboxamide;

Methyl 3-[(3,5-di-tert-butyl-4-hydroxyphenyl)- 2H-1-benzopyran]-7-carboxylate.

According to the present invention, the compounds of formula (I) which are more particularly preferred are those in which at least one, and preferably all, of the conditions below are satisfied:

$R_1$ is a radical —$(CH_2)_p$—CO—O—$R_{14}$;

$R_2$, $R_3$, $R_4$, $R_5$, $R_6$ and $R_9$ are hydrogen atoms;

$R_7$ is a cycloalkyl radical;

$R_8$ is a radical —$OR_{12}$;
Z is an oxygen atom;
Y is a radical $C(R_{11})_2$.

The present invention also features the processes for the preparation of the compounds of formula (I), in particular via the reaction schemes described below and illustrated in the FIGS. 1 and 2 of the Drawings.

Intermediate compounds for the synthesis of the compounds of formula (I) may thus have the following structural formula (IV):

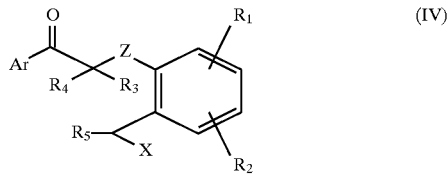

in which $R_1$, $R_2$, $R_3$, $R_4$, $R_5$, Z and Ar are as defined above, and X is a hydrogen atom, a halogen atom or a hydroxyl group.

Among the compounds of formula (IV), particularly representative are the following:

Methyl 4-[(5,6,7,8-tetrahydro-5,5,8,8-tetramethyl-2-naphthoyl)methyloxy]-3-methylbenzoate;

Methyl 4-[(5,6,7,8-tetrahydro-5,5,8,8-tetramethyl-2-naphthoyl)methyloxy]-3-bromomethylbenzoate;

Methyl 3-[(3-(1-adamantyl)-4-methoxybenzoyl) methyloxy]-4-methylbenzoate;

Methyl 3-[(3-(1-adamantyl)-4-methoxybenzoyl) methyloxy]-4-bromomethylbenzoate;

Methyl 3-[(5,6,7,8-tetrahydro-5,5,8,8-tetramethyl-2-naphthoyl)methyloxy]-4-methylbenzoate;

Methyl 3-[(5,6,7,8-tetrahydro-5,5,8,8-tetramethyl-2-naphthoyl)methyloxy]-4-bromomethylbenzoate;

Methyl 3-[(3,5-di-tert-butyl-4-methoxybenzoyl) methyloxy]-4-methylbenzoate;

Methyl 3-[(3,5-di-tert-butyl-4-hydroxybenzoyl) methyloxy]-4-methylbenzoate.

According to the present invention, the compounds of formula (IV) which are more particularly preferred are those in which at least one, and preferably all, of the conditions below are satisfied:

$R_1$ is a radical —$(CH_2)_p$—CO—O—$R_{14}$;
$R_2$, $R_3$, $R_4$, $R_5$, $R_6$ and $R_9$ are hydrogen atoms;
$R_7$ is a cycloalkyl radical;
$R_8$ is a radical —$OR_{12}$;
Z is an oxygen atom;
Y is a radical $C(R_{11})_2$;
X is a hydrogen atom or a halogen atom.

Thus, the compounds of formula (I) may be prepared (FIG. 1) from the ketone (V) by halogenation, for example using a brominating agent such as bromine. The compound (VI) obtained is then coupled with the compound (VII), in the presence of a base such as potassium carbonate or sodium hydride. The coupled derivative (VIII) is halogenated in the benzylic position by the action of a halogenating agent such as an N-bromosuccinimide or an N-chlorosuccinimide. The halide (IV) is converted into a phosphorus ylide by the action of a phosphine such as triphenylphosphine. The phosphonium salt (IX) is cyclized by addition of a base such as sodium methoxide, to produce the compounds (I).

Figure 2:
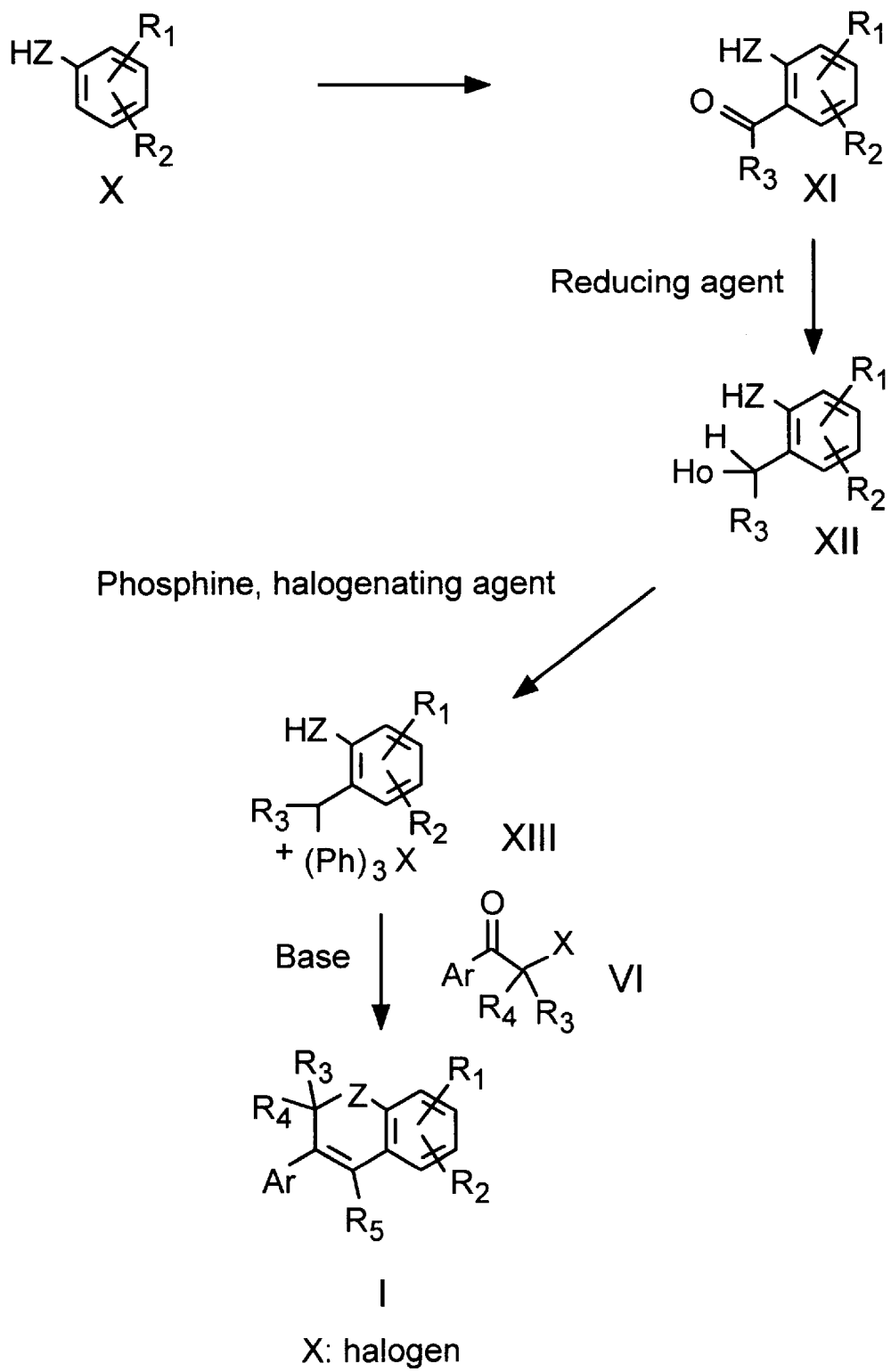
Figure 2:
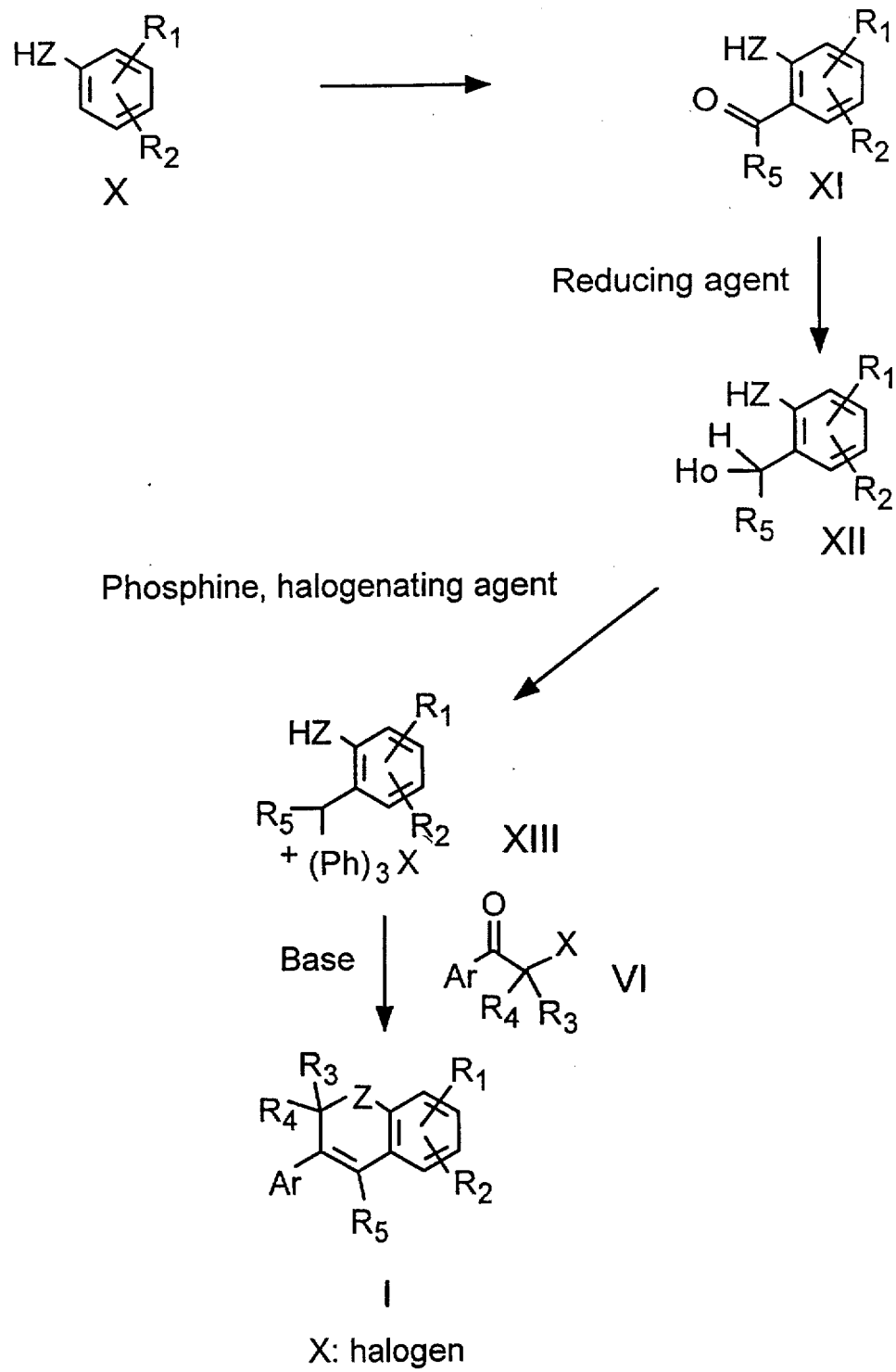

The compounds of formula (I) may also be obtained after coupling and cyclization between the intermediate (VI) and a phosphonium salt (XIII) (FIG. 2). In this event, the derivative (XIII) is obtained according to the sequence described below. For example, by aromatic formulation, using hexamethyltetramine in trifluoroacetic acid, of the compound (X), the compound (XI) is obtained. The carbonyl derivative (XI) is then reduced by the action of a reducing agent such as sodium borohydride, to give the compound (XII). The phosphonium salt (XIII) is obtained by the action of phosphine in the presence of a halogenating agent such as $CBr_4$ or hydrobromic acid. The condensation and cyclization is carried out in the presence of a base.

The compounds of formula (I) are themselves starting materials for the preparation of other useful derivatives thereof. These derivatives are obtained via standard synthetic techniques employed in chemistry, such as those described in *Advanced Organic Chemistry* by J. March; John Wiley and Sons (1985).

For example, functional modifications of the group $R_1$ may be carried out, as indicated below:

| | |
|---|---|
| Carboxylic acid | → Ester |
| Ester | → Carboxylic acid |
| Acid | → Acid chloride |
| Acid chloride | → Amide |
| Acid | → Amide |
| Acid | → Alcohol |
| Alcohol | → Aldehyde |
| Amide | → Amine |
| Thiol | → Thioether |
| Thioether | → Sulfoxide |
| Thioether | → Sulfone |
| Sulfonic acid | → Sulfonic ester |
| Sulfonic acid | → Sulfonamide |
| Sulfinic acid | → Sulfinic ester |

The compounds of formula (I) exhibit agonist or antagonist activity with respect to the expression of one or more biological markers in the test for differentiation of mouse embryonic teratocarcinoma cells (F9) (*Skin Pharmacol.*, 3, p. 256–267 (1990)) and/or on the in vitro differentiation of human keratinocytes (*Skin Pharmacol.*, 3, p. 70–85 (1990)) in response to a treatment by retinoids. The aforesaid tests demonstrate the activities of the subject compounds in the fields of cell differentiation and proliferation. Their activities may also be measured in tests of cell transactivation using pretransfected recombinant RAR or RXR receptors (B. A. Bernard et al, *Biochemical and Biophysical Research Communication*, vol. 186, 977–983 (1992); M. F. Boehm et al, *Journal of Medicinal Chemistry*, 37, 408–414 (1994)).

The present invention also features therapeutic/pharmaceutical applications of the compounds of formula (I).

The compounds according to the invention are particularly suitable in the following fields of therapy:

(1) for treating dermatological conditions associated with a keratinization disorder related to differentiation and to proliferation, especially for treating acne vulgaris or comedo-type, polymorphic or rosacea acnes, nodulocystic acne or acne conglobata, senile acnes, secondary acnes such as solar acne, acne medicamentosa or occupational acne;

(2) for treating other types of keratinization disorders, especially ichthyoses, ichthyosiform states, Darier's disease, keratoses palmaris and plantaris, leucoplakias and leucoplakia-like states, skin or mucous (buccal) lichen;

(3) for treating other dermatological conditions associated with a keratinization disorder manifesting an inflammatory and/or immunoallergic component, and, especially, all forms of psoriasis, whether cutaneous, mucous or ungual, and even arthropathic psoriasis, or, alternatively, skin atopy, such as eczema or respiratory atopy or alternatively gingival hypertrophy; the compounds can also be used for treating inflammatory conditions not exhibiting keratinization disorder;

(4) for treating all dermal or epidermal proliferations, whether benign or malignant, whether or not they are of viral origin, such as verruca vulgaris, verruca plana and epidermodysplasia verruciformis, oral or florid papillomatoses and proliferations which can be induced by ultraviolet radiation, especially in the case of baso- and spinocellular epitheliomas;

(5) for treating other dermatological disorders such as bullous dermatoses and collagen diseases;

(6) for treating certain ophthalmological disorders, especially corneopathies;

(7) for repairing or combating skin aging, whether photoinduced or chronologic, or to reduce pigmentations and actinic keratoses, or all pathologies associated with chronologic or actinic aging;

(8) for preventing or curing the stigmas of epidermal and/or dermal atrophy induced by local or systolic corticosteroids, or any other form of skin atrophy;

(9) for preventing or treating cicatrization disorders or for preventing or for repairing vibices;

(10) for combating disorders of the sebaceous function, such as acne hyperseborrhoea or simple seborrhoea;

(11) for the treatment or prevention of cancerous or precancerous states;

(12) for the treatment of inflammatory conditions such as arthritis;

(13) for the treatment of any condition of viral origin at the level of the skin or in general;

(14) for the prevention or treatment of alopecia;

(15) for the treatment of dermatological or general conditions including an immunological component;

(16) for the treatment of conditions of the cardiovascular system, such as arteriosclerosis.

For the aforesaid therapeutic or pharmaceutical applications, the compounds according to the invention can advantageously be used in combination with other compounds displaying retinoid-type activity, with the D vitamins or derivatives thereof, with corticosteroids or estrogens, with antioxidants, with anti-free radical agents, with $\alpha$-hydroxy or $\alpha$-keto acids or derivatives thereof, or alternatively with ion (e.g., potassium) channel blockers.

Exemplary of the other retinoids which can thus be used are all-trans retinoic acid, 9-cis retinoic acid, or a synthetic analog which binds to RXR or RAR type receptors.

By "D vitamins or derivatives thereof" are intended, for example, the derivatives of vitamin $D_2$ or $D_3$ and in particular 1,25-dihydroxyvitamin $D_3$. By "anti-free radical agents" are intended, for example, $\alpha$-tocopherol, superoxide dismutase, ubiquinol or certain metal-chelating agents. By "$\alpha$-hydroxy or $\alpha$-keto acids or derivatives thereof" are intended, for example, lactic, maleic, citric, glycolic, mandelic, tartaric, glyceric, ascorbic or salicylic acids or salts, amides or esters thereof. By "ion channel blockers" are intended, for example, Minoxidil (2,4-diamino-6-piperidinopyrimidine 3-oxide) and derivatives thereof.

The present invention thus also features medicinal compositions containing at least one compound of formula (I), one of its optical or geometric isomers, or one of its pharmaceutically acceptable salts or other derivatives thereof.

The pharmaceutical/therapeutic compositions of this invention, intended especially for the treatment of the aforesaid disease states comprise a carrier, diluent or vehicle which is pharmaceutically acceptable and compatible with the mode or regime of administration selected for the given composition, at least one compound of formula (I), one of its optical or geometric isomers or one of the salts, etc., thereof.

The administration of the compounds according to the invention can be carried out systemically, enterally, parenterally, topically or ocularly.

For enteral administration, the medicinal/pharmaceutical compositions may be in the form of tablets, gelatin capsules, sugar-coated tablets, syrups, suspensions, solutions, elixirs, powders, granules, emulsions, microspheres or nanospheres or lipid or polymeric vesicles which permit a controlled release. For parenteral administration, the compositions may be in the form of solutions or suspensions for perfusion or for injection.

The compounds according to the invention are generally administered at a daily dose of about 0.01 mg/kg to 100 mg/kg of body weight, and this at the regime or rate of 1 to 3 doses per diem.

For topical administration, the pharmaceutical compositions based on compounds according to the invention are more particularly intended for the treatment of the skin and the mucous membranes and can be provided in the form of ointments, creams, milks, pommades, salves, powders, impregnated pads, solutions, gels, sprays, lotions or suspensions. They may also be provided in the form of microspheres or nanospheres or lipid or polymeric vesicles or polymeric patches and hydrogels which permit a controlled release.

These compositions for topical administration may, moreover, be provided either in anhydrous form or in an aqueous form according to the particular clinical indication.

For ocular administration, they are principally collyria.

These compositions for topical or ocular application contain at least one compound of formula (I), or one of its optical or geometric isomers or, alternatively, one of its salts, etc., at a concentration preferably ranging from 0.00% to 5% by weight relative to the total weight of the composition.

The compounds of formula (I) according to the invention also find application in the cosmetic field, in particular for body and hair care and especially for the treatment of skins with acne tendency, for hair regrowth, to prevent hair loss, for combating the greasy appearance of the skin or the hair, in the protection against the harmful effects of the sun or in the treatment of physiologically dry skins, for preventing and/or for combating photoinduced or chronologic aging.

For cosmetic applications, the compositions of the invention may, moreover, be advantageously used in combination with other compounds displaying retinoid-type activity, with the D vitamins or derivatives thereof, with corticosteroids or estrogens, with anti-free radical agents, with antioxidants, with $\alpha$-hydroxy or $\alpha$-keto acids or derivatives thereof, or alternatively with ion channel blockers, all of these different active agents being as defined above.

The present invention therefore also features cosmetic compositions comprising a carrier, diluent or vehicle which is cosmetically acceptable and suitable for a topical application, at least one compound of formula (I) or one of its optical or geometric isomers or one of its salts. Such cosmetic compositions are advantageously presented in the form of a cream, a milk, a lotion, a gel, microspheres or nanospheres or lipid or polymeric vesicles, a soap or a shampoo.

The concentration of the compound of formula (I) in the cosmetic compositions according to the invention advantageously ranges from 0.001% to 3% by weight relative to the total composition.

The medicinal and cosmetic compositions according to the invention may, in addition, contain inert or even pharmacodynamically or cosmetically active additives and adjuvants, or combinations of these additives, and, especially: wetting agents; depigmenting agents such as hydroquinone, azelaic acid, caffeic acid or kojic acid; emollients; moisturizing agents such as glycerol, PEG 400, thiamorpholinone and its derivatives or alternatively urea; antiseborrhoeic or antiacne agents such as S-carboxymethylcysteine, S-benzylcysteamine, salts or derivatives thereof, benzoyl peroxide; antibiotics such as erythromycin and esters thereof, neomycin, clindamycin and esters thereof, tetracyclines; antifungal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazine-1,1-dioxide) and Phenytoin (5,4-diphenyl-2,4-imidazolidinedione); non-steroidal anti-inflammatory agents; carotenoids and especially β-carotene; anti-psoriatic agents such as anthralin and derivatives thereof; and, lastly, 5,8,11,14-eicosatetraynoic and 5,8,11-eicosatrynoic acids and esters and amides thereof.

The compositions according to the invention may also contain taste- or flavor-enhancing agents, preservatives such as para-hydroxybenzoic acid esters, stabilizing agents, moisture regulating agents, pH regulating agents, osmotic pressure modifying agents, emulsifying agents, UV-A and UV-B screening agents, antioxidants such as a-tocopherol, butylated hydroxyanisole or butylated hydroxytoluene.

In order to further illustrate the present invention and the advantages thereof, the following specific examples are given, it being understood that same are intended only as illustrative and in nowise limitative.

In said examples to follow, as in the above description, all parts and percentages are given by weight, unless otherwise indicated.

EXAMPLES

A. Examples of preparation of compounds via the synthetic route shown in FIG. 1:

EXAMPLE 1

Synthesis of 3-[(3-(1-adamantyl)-4-methoxyphenyl)-2H-1-benzopyran]-7-carboxylic acid:

(a) Preparation of 3-adamantyl-4-methoxyacetophenone:

3-adamantyl-4-methoxybenzoic acid (50 g, 0.17 mol) was heated to 50° C. in toluene. Thionyl chloride (25 ml, 0.34 mol) was then added. After heating for two hours at reflux, the mixture was concentrated to dryness.

Tetramethyltin (6 ml) was added dropwise to a solution of 3-adamantyl-4-methoxybenzoyl chloride (12 g, 39 mmol) in hexamethylphosphorus triamide (45 ml). BnPd(PPh$_3$)$_2$Cl (30 mg, 398 mmol) was then introduced. The mixture was heated at 65° C. for one hour and then maintained under stirring for two days at room temperature. After extraction with ether, washing with water and drying over sodium sulfate, the organic phase was concentrated on a rotary evaporator under vacuum. The product was purified by flash chromatography (65% CH$_2$Cl$_2$, 35% hexane). Its properties were as follows:
White solid. Mass: 6.67 g. Yield: 60%.
$^1$H NMR (CDCl$_3$, 250 MHz); 1.77 (6H, s), 2.10 (9H, s), 2.56 (3H, s), 3.90 (3H, s), 6.88 (1H, Ar, d), 7.82 (1H, Ar, m), 7.88 (1H, Ar, d)

(b) Preparation of 3-adamantyl-4-methoxybromo-acetophenone:

3-adamantyl-4-methoxyacetophenone (11.41 g, 40 mmol) was dissolved in 60 ml of dioxane and 60 ml of ethyl ether. Bromine (2.3 ml, 45 mmol) diluted in 20 ml of dichloromethane was added dropwise. The mixture was stirred for one hour at room temperature. The reaction medium was poured into 100 ml of an ice-water mixture. After stirring and separation of the phases once settling had taken place, the organic phase was washed twice with 100 ml of water, dried over magnesium sulfate and concentrated on a rotary evaporator under vacuum at 40° C. The product was purified by flash chromatography on a column of silica (CH$_2$Cl$_2$). Its properties were as follows:
White solid. Mass: 14.52 g. Yield: quantitative.
$^1$H NMR (CDCl$_3$, 250 MHz); 1.78 (6H, s), 2.09 (9H, s), 3.92 (3H, s), 4.41 (2H, s), 6.91 (1H, Ar, d), 7.86 (1H, Ar, m), 7.91 (1H, Ar, d).

(c) Preparation of methyl 3-[(3-(1-adamantyl)-4-methoxybenzoyl)methyloxy]-4-methylbenzoate:

A solution of 3-adamantyl-4-methoxybromoacetophenone (1 g, 2.74 mmol), methyl 3-hydroxy-4-methylbenzoate (0.46 g, 2.74 mmol) and potassium carbonate (0.38 g, 2.74 mmol) in methyl ethyl ketone (20 ml) was heated at reflux for three hours. The reaction medium was filtered, followed by addition of 40 ml of water and 40 ml of ethyl ether. After stirring and separation of the phases once settling had taken place, the organic phase was washed twice with 40 ml of water, dried over magnesium sulfate and concentrated on a rotary evaporator under vacuum at 40° C. The product was purified by flash chromatography on a column of silica (30% ethyl acetate, 70% heptane). Its properties were as follows:
White solid. Mass: 1.07 g. Yield: 87%. m.p.: 143° C.
$^1$H NMR (CDCl$_3$, 250 MHz) ; 1.77 (6H, s), 2.09 (9H, s), 2.47 (3H, s), 3.88 (3H, s), 3.92 (3H, s), 5.31 (2H, s), 6.92 (1H, Ar, d), 7.22 (1H, Ar, d) 7.43 (1H, Ar, s), 7.59 (1H, Ar, s), 7.88 (2H, m).

(d) Preparation of methyl 3-[(3-(1-adamantyl)-4-methoxybenzoyl)methyloxy]-4-bromomethylbenzoate:

A solution of methyl 3[(3-(1-adamantyl)-4-methoxybenzoyl)methyloxy]-4-methylbenzoate (2.36 g, 5.26 mmol) and benzoyl peroxide (0.02 g) in carbon tetrachloride (50 ml) was heated to reflux. Benzoyl peroxide (0.03 g) and N-bromosuccinimide (1.05 g, 5.9 mmol) were added. The mixture was heated for four hours at reflux. 50 ml of water and 50 ml of dichloromethane were added. After separation of the phases once settling had taken place, the organic phase was washed twice with 50 ml of water and dried over magnesium sulfate. After concentration on a rotary evaporator at 40° C. under vacuum, the desired product was isolated by flash chromatography (CH$_2$Cl$_2$). Its properties were as follows:
White solid. Mass: 1.8 g. Yield: 34%. m.p.: 165° C.
$^1$H NMR (CDCl$_3$, 250 MHz) : 1.78 (6H, s), 2.10 (9H, s), 3.89 (3H, s), 3.93 (3H, s), 4.66 (2H, s), 5.42 (2H, s), 6.93 (1H, Ar, d), 7.44 (2H, Ar, m), 7.65 (1H, Ar, d), 7.89 (2H, m).

(e) Preparation of methyl 3-[(3-(1-adamantyl)-4-methoxyphenyl)-2H-1-benzopyran]-7-carboxylate:

A mixture of methyl 3-[(3-(1-adamantyl)-4-methoxybenzoyl)methyloxy]-4-bromomethylbenzoate (0.53 g, 1 mmol) and triphenylphosphine (0.29 g, 1.1 mmol) in tetrahydrofuran (5 ml) was heated at reflux for 4 hours under argon. The mixture was cooled to room temperature and a 30% solution of sodium methoxide in methanol (0.18 g, 1 mmol) was added dropwise. The mixture was stirred for thirty minutes at room temperature. The solvent was evaporated off on a rotary evaporator under vacuum. 20 ml of water and 80 ml of dichloromethane were added. The organic phase was washed twice with 20 ml of saturated sodium chloride solution and dried over magnesium sulfate. After concentration on a rotary evaporator at 40° C. under vacuum, the solid obtained was washed in ethanol. Its properties were as follows:

White solid. Mass: 0.3 g. Yield: 70%. m.p.: 209° C.

$^1$H NMR (CDCl$_3$, 250 MHz): 1.79 (6H, s), 2.12 (9H, s), 3.87 (3H, s), 3.90 (3H, s), 5.19 (2H, s), 6.73 (1H, s), 6.89 (1H, Ar, d), 7.11 (1H Ar, d), 7.24 (1H, Ar, d), 7.36 (1H, Ar, s), 7.48 (1H, Ar, s), 7.59 (1H, Ar, d).

(f) Synthesis of 3-[(3-(1-adamantyl)-4-methoxyphenyl)-2H-1-benzopyran]-7-carboxylic acid:

A solution of methyl 3-[(3-(1-adamantyl)-4-methoxyphenyl)-2H-1-benzopyran]-7-carboxylate (0.12 g, 0.28 mmol) and sodium hydroxide (11 mg, 1.5 mmol) in methanol (1.5 ml) was heated for twelve hours at reflux. The methanol was removed by distillation on a rotary evaporator. 3 ml of water were added and the mixture was acidified to pH=1 with 32% hydrochloric acid solution. After filtration, the solid obtained was washed in hexane and dried under vacuum at 40° C. Its properties were as follows:

Light-yellow solid. Mass: 0.1 g. Yield: 86%

$^1$H NMR (DMSO, 250 MHz): 1.75 (6H, s), 2.09 (9H, s), 2.47 (3H, s), 3.84 (3H, s), 5.21 (2H, s), 6.61 (1H, s), 6.87 (1H, Ar, s), 7.01 (1H, Ar, d), 7.27 (1H, Ar, d), 7.38 (2H, Ar, m) , 7.49 (H, d).

EXAMPLE 2

Synthesis of 3-[(5,6,7,8-tetrahydro-5,5,8,8-tetramethyl-2-naphthyl)-2H-1-benzopyran]-7-carboxylic acid:

(a) Preparation of methyl 3-[(5,6,7,8-tetrahydro-5,5,8,8-tetramethyl-2-naphthoyl)methyloxy]-4-methylbenzoate:

A solution of 5,6,7,8-tetrahydro-5,5,8,8-tetramethyl-2-bromoacetonaphthone (1 g, 2.74 mmol), methyl 3-hydroxy-4-methylbenzoate (0.46 g, 2.74 mmol) and potassium carbonate (0.38 g, 2.74 mmol) in methyl ethyl ketone (20 ml) was heated at reflux for three hours. The reaction medium was filtered, followed by addition of 40 ml of water and 40 ml of ethyl ether. After stirring and separation of the phases once settling had taken place, the organic phase was washed twice with 40 ml of water, dried over magnesium sulfate and concentrated on a rotary evaporator under vacuum at 40° C. The product was purified by flash chromatography on a column of silica (30% ethyl acetate, 70% heptane). Its properties were as follows:

White solid. Mass: 1.07 g. Yield: 87%. m.p.: 99° C.

$^1$H NMR (CDCl$_3$, 250 MHz) : 1.31 (6H, s), 1.32 (6H, s), 1.71 (4H, s), 2.35 (3H, s), 3.87 (3H, s), 5.25 (2H, s), 7.18 (1H, Ar, d), 7.36 (2H, Ar, m), 7.54 (1H, Ar, q), 7.69 (1H, Ar, q) , 7.92 (1H, Ar, s)

(b) Preparation of methyl 3-[(5,6,7,8-tetrahydro-5,5,8,8-tetramethyl-2-naphthoyl)methyloxy]-4-bromomethylbenzoate:

A solution of methyl 3-[(5,6,7,8-tetrahydro-5,5,8,8-tetramethyl-2-naphthoyl)methyloxy]-4-methylbenzoate (7.02 g, 16.7 mmol), benzoyl peroxide (0.02 g) and N-bromosuccinimide (4.28 g, 24 mmol) in carbon tetrachloride (370 ml) was heated at reflux and irradiated with a 1000 W lamp for forty five minutes. 350 ml of water and 250 ml of dichloromethane were added. After separation of the phases once settling had taken place, the organic phase was washed twice with 350 ml of water and dried over magnesium sulfate. After concentration on a rotary evaporator at 40° C. under vacuum, the three products obtained were purified by flash chromatography (CH$_2$Cl$_2$) and then by HPLC (70% CH$_2$Cl$_2$, 30% heptane). The properties of the monobromo benzyl compound were as follows:

White solid. Mass: 1.02 g. Yield: 12.3 w. m.p.: 142° C.

$^1$H NMR (CDCl$_3$, 250 MHz): 1.20 (12H, s), 1.66 (4H, s), 3.82 (3H, s), 4.61 (2H, s), 5.40 (2H, s), 7.37 (2H, Ar, m), 7.59 (1H, Ar, q), 7.67 (1H, Ar, q), 7.90 (1H, Ar, s).

(c) Preparation of methyl 3-[(5,6,7,8-tetrahydro-5,5,8,8-tetramethyl-2-naphthyl)-2H-1-benzopyran]-7-carboxylate:

A mixture of methyl $^3$-[(5,6,7,8-tetrahydro-5,5,8,8-tetramethyl-2-naphthoyl)methyloxy]-4-bromomethylbenzoate (1 g, 2.01 mmol) and triphenylphosphine (0.59 g, 2.21 mmol) in tetrahydrofuran (12 ml) was heated at reflux for four hours under argon. The mixture was cooled to room temperature and a 30% solution of sodium methoxide in methanol (0.37 g, 2.05 mmol) was added dropwise. The mixture was stirred for thirty minutes at room temperature. The solvent was evaporated off on a rotary evaporator under vacuum. 20 ml of water and 80 ml of ethyl acetate were added. The organic phase was washed twice with 20 ml of saturated sodium chloride solution and dried over magnesium sulfate. After concentration on a rotary evaporator at 40° C. under vacuum, the solid obtained was washed with heptane. Its properties were as follows:

White solid. Mass: 0.6 g. Yield: 79%. m.p.: 154° C.

$^1$H NMR (CDCl$_3$, 250 MHz) : 1.29 (6H, s), 1.32 (6H, s), 1.70 (4H, s), 3.90 (3H, s), 5.20 (2H, s), 6.77 (1H, s), 7.12 (1H, Ar, d), 7.22 (1H, Ar, q), 7.33 (1H, Ar, s), 7.37 (1H, Ar, s), 7.49 (1H, Ar, s), 7.59 (1H, Ar, s).

(d) Synthesis of 3-[(5,6,7,8-tetrahydro-5,5,8,8-tetramethyl-2-naphthyl)-2H-1-benzopyran]-7-carboxylic acid:

A solution of methyl $^3$-[(5,6,7,8-tetrahydro-5,5,8,8-tetramethyl-2-naphthyl)-2H-1-benzopyran]-7-carboxylate (0.6 g, 1.6 mmol), sodium hydroxide (0.38 g, 9.5 mmol), methanol (1 ml) and water (1 ml) in THF (9 ml) was stirred for twenty four hours. The reaction medium was concentrated on a rotary evaporator. 10 ml of water were added and the mixture was acidified to pH=1 with 32% hydrochloric acid solution. After filtration, the solid obtained was dissolved in a mixture of 25 ml of ethyl acetate and 10 ml of heptane. The ethyl acetate was distilled off on a rotary evaporator under vacuum, at 40° C. The product was collected by filtration. Its properties were as follows:

White solid. Mass: 0.489 g. Yield: 84%. m.p.: 285° C.

$^1$H NMR (DMSO, 250 MHz): 1.15 (6H, s), 1.2 (6H, s), 1.56 (4H, s), 5.15 (2H, s), 6.99 (1H, s), 7.24 (4H, Ar, m), 7.41 (2H, Ar, m), 12.78 (1H, s).

EXAMPLE 3

Synthesis of 3-[(5,6,7,8-tetrahydro-5,5,8,8-tetramethyl-2-naphthyl)-2H-1-benzopyran]-6-carboxylic acid:

(a) Preparation of methyl 4-[(5,6,7,8-tetrahydro-5,5,8,8-tetramethyl-2-naphthoyl)methyloxy]-3-methylbenzoate:

A solution of methyl 5,6,7,8-tetrahydro-5,5,8,8-tetramethyl-2-bromoacetonaphthone (5 g, 16.2 mmol), methyl 4-hydroxy-3-methylbenzoate (2.68 g, 16.1 mmol) and potassium carbonate (2.23 g, 16.1 mmol) in methyl ethyl ketone (120 ml) was heated at reflux for three hours. The reaction medium was filtered, followed by addition of 250 ml of water and 250 ml of ethyl ether. After stirring and separation of the phases once settling had taken place, the organic phase was washed twice with 40 ml of water, dried over magnesium sulfate and concentrated on a rotary evaporator under vacuum at 40° C. The product was purified by flash chromatography on a column of silica (30% ethyl acetate, 70% heptane). Its properties were as follows:

White solid. Mass: 5.35 g. Yield: 84%. m.p.: 111° C.

$^1$H NMR (CDCl$_3$, 250 MHz): 1.31 (12H, s), 1.71 (4H, s), 2.34 (3H, s), 3.87 (3H, s), 5.34 (2H, s), 6.71 (1H, Ar, d), 7.42 (1H, Ar, d) , 7.73 (1H, Ar, q), 7.82 (1H, Ar, q), 7.86 (1H, Ar, d) , 7.98 (1H, Ar, d)

(b) Preparation of methyl 4-[(5,6,7,8-tetrahydro-5,5,8,8-tetramethyl-2-naphthoyl)methyloxy]-3-bromomethylbenzoate:

A solution of methyl 4-[(5,6,7,8-tetrahydro-5,5,8,8-tetramethyl-2-naphthoyl)methyloxy]-3-methylbenzoate (3.73 g, 9.5 mmol), benzoyl peroxide (0.02 g) and N-bromosuccinimide (1.74 g, 9.8 mmol) in carbon tetrachloride (200 ml) was heated to reflux and irradiated with a 1000 W lamp for fifteen minutes. 300 ml of water and 150 ml of dichloromethane were added. After separation of the phases once settling had taken place, the organic phase was washed twice, with 250 ml of water, and dried over magnesium sulfate. After concentration on a rotary evaporator at 40° C. under vacuum, the product obtained was purified by flash chromatography (10% $CH_2Cl_2$, 90% heptane). Its properties were as follows:

White solid. Mass: 0.49 g. Yield: 10%. m.p.: 114° C.

$^1$H NMR ($CDCl_3$, 250 MHz) : 1.31 (12H, s) , 1.72 (4H, s), 3.88 (3H, s), 4.65 (2H, s), 5.46 (2H, s), 6.76 (2H, Ar, d), 7.74 (1H, Ar, q), 7.93 (1H, Ar, q), 7.96 (1H, Ar, d), 8.08 (1H, Ar, d).

(c) Preparation of methyl 3-[(5,6,7,8-tetrahydro-5,5,8,8-tetramethyl-2-naphthyl)-2H-1-benzopyran]-6-carboxylate:

A mixture of methyl $^4$-[(5,6,7,8-tetrahydro-5,5,8,8-tetramethyl-2-naphthoyl)methyloxy]-3-bromomethylbenzoate (440 mg, 0.88 mmol) and triphenylphosphine (0.26 g, 1 mmol) in tetrahydrofuran (5 ml) was heated at reflux for four hours, under argon. The mixture was cooled to room temperature and a 30% solution of sodium methoxide in methanol (0.16 g, 0.89 mmol) was added dropwise. The mixture was stirred for 40 minutes at room temperature. The solvent was evaporated off on a rotary evaporator under vacuum. 40 ml of water and 60 ml of ethyl ether were added. The organic phase was washed twice with 40 ml of water and dried over magnesium sulfate. After concentration on a rotary evaporator at 40° C. under vacuum, the solid obtained was washed with heptane. Its properties were as follows:

White solid. Mass: 0.24 g. Yield: 72w. m.p.: 144° C.

$^1$H NMR ($CDCl_3$, 250 MHz) : 1.29 (6H, s) , 1.32 (6H, s) , 1.70 (4H, s), 3.89 (3H, s), 5.42 (2H, s), 6.77 (1H, s), 6.84 (1H, Ar, d), 7.20 (1H, Ar, q), 7.34 (1H, Ar, d), 7.78 (1H, Ar, d) 7.81 (1H, Ar, q).

(d) Synthesis of 3-[(5,6.7.8-tetrahydro-5,5,8,8-tetramethyl-2-naphthyl)-2H-1-benzopyran]-6-carboxylic acid:

A solution of methyl 4-[(5,6,7,8-tetrahydro-5,5,8,8-tetramethyl-2-naphthyl)-2H-1-benzopyran]6-carboxylate (0.22 g, 0.58 mmol), sodium hydroxide (0.1 g, 2.5 mmol), methanol (0.5 ml) and water (0.5 ml) in THF (3 ml) was heated for four hours at reflux. The reaction medium was concentrated on a rotary evaporator. 5 ml of water were added and the mixture was acidified to pH=1 with 32% hydrochloric acid solution. After filtration, the solid obtained was dissolved in a mixture of 10 ml of ethyl acetate, 10 ml of THF and 10 ml of heptane. The mixture was concentrated on a rotary evaporator under vacuum, at 40° C. The product was collected by filtration. Its properties were as follows:

White solid. Mass: 0.210 g. Yield: quantitative. m.p.: 271° C.

$^1$H NMR (DMSO, 250 MHz): 1.26 (6H, s), 1.31 (6H, s), 1.67 (4H, s), 5.29 (2H, s), 6.89 (1H, Ar, d), 7.13 (1H, s), 7.31 (1H, Ar, d), 7.38 (1H, Ar, d), 7.52 (1H, Ar, s), 7.73 (1H, Ar, d) 7.82 (1H, Ar, s).

B. Examples of preparation of compounds via the synthetic route shown in FIG. 2:

EXAMPLE 4

Synthesis of methyl 3-[(3-(1-adamantyl)-4-methoxyphenyl)-2H-1-benzopyran]-6-carboxylate:

(a) Preparation of methyl 3-formyl-4-hydroxybenzoate:

Methyl-4-hydroxybenzoate (4.56 g, 30 mmol) was mixed with trifluoroacetic acid (24 ml) and hexamethylenetetramine (8.41 g, 60 mmol) (Duff reaction). The reaction medium was heated to 80° C. for three hours and cooled to 0° C., followed by successive addition of 15 ml of 50% sulfuric acid and 90 ml of demineralized water. After stirring for one hour at room temperature, the medium was extracted with ethyl ether, washed with water, dried over magnesium sulfate and filtered, and the solvents were evaporated off. The product was purified by passage through a column of silica and was eluted with dichloromethane. After evaporation of the solvents, 1.92 g of a crystallized white solid are obtained, equivalent to a yield of 36%. Its properties were as follows:

White solid. Mass : 1.92 g. Yield : 36%.

$^1$H NMR ($CDCl_3$, 250 Mhz) : 3.93 (3H, s), 7.04 (1H, Ar, d) 8.19 (1H, Ar, Dd), 8.32 (1H, Ar, d), 11.40 (1H, s), 9.96 (1H, s).

(b) Preparation of methyl 3-hydroxymethyl-4-hydroxybenzoate:

The compound obtained in (a) (1.80 g, 10 mmol) was mixed with 50 ml of methanol, and sodium borohydride (189 mg, 5 mmol) was added portionwise while maintaining the temperature below 20° C. After stirring for 5 minutes at room temperature, the methanol was evaporated off and the medium was then poured onto a 6N HCl/ice mixture, extracted with ethyl ether, washed with water to neutral pH, dried over magnesium sulfate and filtered, and the solvents were evaporated off. The properties of the final product were as follows:

White solid. Mass : 1.46 g. Yield : 82%.

$^1$H NMR (DMSO, 250 Mhz) : 3.80 (3H, s), 4.49 (2H, s), 5.14 (1H, s), 6.86 (1H, Ar, d), 7.71 (1H, Ar, Dd), 7.98 (1H, Ar, d) , 10.31 (1H, s).

(c) Preparation of 2-hydroxy-5-methoxycarbonylbenzyl triphenylphosphonium bromide:

The compound obtained in (b) (182 mg, 1 mmol) was mixed successively with 2 ml of acetonitrile and triphenylphosphine hydrobromide (361 mg, 1.05 mmol). After heating at reflux for one hour fifteen minutes, the reaction medium was cooled and evaporated to dryness, ethyl ether was added, the mixture was filtered and the precipitate was washed with ethyl ether. After drying in an oven, 470 mg of a white solid were obtained, equivalent to a yield of 93%. Its properties were as follows:

White solid. Mass : 470 mg. Yield : 93%.

$^1$H NMR (DMSO, 250 Mhz) : 3.70 (3H, s), 5.00 (2H, d), 6.83 (1H, Ar, d), 7.40–7.92 (20H, Ar, m), 10.79 (1H, s).

(d) Synthesis of methyl 3-[(3-(1-adamantyl)-4-methoxyohenyl)-2H-1-benzopyran]-6-carboxylate:

A solution of sodium methoxide (0.45 ml, 2.36 mmol) was added dropwise to a solution of 2-hydroxy-5-methoxycarbonylbenzyl triphenylphosphonium bromide (1.52 g, 3 mmol) in THF (20 ml). The mixture was maintained under stirring at room temperature for 20 minutes, followed by addition of 3-(1-adamantyl)-4-methoxybromoacetophenone (1.1 g, 3 mmol). The mixture was stirred at room temperature for thirty minutes. A solution of sodium methoxide (0.84 ml, 4.41 mmol) was added dropwise. The mixture was heated at reflux for six hours. The reaction medium was concentrated on a rotary evaporator under vacuum at 40° C. 20 ml of water were added and the mixture was then acidified with concentrated hydrochloric acid solution to pH=1. This mixture was extracted with 30 ml of ethyl acetate. After separation of the phases once settling had taken place, the organic phase was washed twice with 20 ml of water, dried over anhydrous magnesium sulfate and concentrated on a rotary evaporator under vacuum at 40° C. Its properties were as follows:

White solid. Mass: 418 mg. Yield: 32%. m.p.: 162° C.

$^1$H NMR (DMSO, 250 MHz): 1.75 (6H, s), 2.08 (9H, s), 3.82 (6H, s), 5.27 (2H, s), 6.89 (1H, Ar, d, J=10 Hz), 7.00 (1H, Ar, d, J=10 Hz), 7.07 (1H, s), 7.35 (2H, Ar, m), 7.71 (1H, Ar, dd, J=1.9 Hz, J=8.5 Hz), 7.83 (1H, Ar, d, 1.9 Hz).

$^3$C NMR (DMSO, 250 MHz): 28.50, 36.66, 36.74, 40.10, 51.94, 55.43, 67.09, 112.26, 115.23, 116.37, 122.81, 122.91, 123.04, 123.76, 127.48, 128.11, 130.12, 132.25, 137.93, 156.68, 158.68, 158.96, 165.95.

EXAMPLE 5

Sythnesis of 3-[(3-(1-adamantyl)-4-methoxyphenyl)-2H-1-benzopyran]-6-carboxylic acid:

A solution of methyl 3-[(3-(1-adamantyl)-4-methoxyphenyl)-2H-1-benzopyran]-6-carboxylate (0.12 g, 1.28 mmol) and sodium hydroxide (11 mg, 1.5 mmol) in methanol (2 ml) was heated for 12 hours at reflux. The methanol was removed by distillation on a rotary evaporator under vacuum. 3 ml of water were added and the mixture was acidified to pH=1 with concentrated hydrochloric acid solution. After filtration, the solid obtained was washed with hexane and oven-dried. Its properties were as follows:

Light-yellow solid. Mass: 100 mg. Yield: 86%. m.p.: 259° C.

$^1$H NMR (DMSO, 250 MHz): 1.74 (6H, s), 2.07 (9H, s), 3.82 (3H, s), 5.26 (2H, s), 6.89 (1H, d, J=8.4 Hz), 6.98 to 7.05 (2H, Ar, m), 7.35 (2H, Ar, m), 7.69 (1H, Ar, d, J=8.2Hz), 7.81 (1H, Ar, s).

$^{13}$C NMR (DMSO, 250 MHz): 28.41, 36.57, 40.21, 55.35, 66.96, 112.21, 114.98, 116.52, 122.67, 122.95, 123.69, 123.92, 127.53, 128.25, 130.21, 132.06, 137.84, 156.30, 158.83, 166.97.

EXAMPLE 6

Synthesis of methyl 3-[(3,5-di-tert-butyl-4-hydroxyphenyl) -2H-1-benzopyran]-6-carboxylate:

(a) Preparation of 3,5-di-tert-butyl-4-hydroxybromoacetophenone:

A solution of 3,5-di-tert-butyl-4-hydroxyacetophenone (2.9 g, 11.5 mmol) in ethyl acetate (70 ml) was added dropwise to a suspension of cuprous bromide (5.2 g, 23 mmol) in dichloromethane at reflux. The mixture was heated for 3 h, filtered and concentrated on a rotary evaporator under vacuum at 40° C. Its properties were as follows:

Violet solid. Mass: 2.93 g. Yield: 78%. m.p.: 104.2° C.

$^1$H NMR (CDCl$_3$, 250 MHz): 1.47 (18H, s), 4.40 (2H, s), 5.92 (1H, s), 7.88 (H, Ar, s).

(b) Synthesis of methyl 3-[(3,5-di-tert-butyl-4-hydroxyophenyl)-2H-1-benzopyran]-6-carboxylate:

A suspension of 2 hydroxy-5-methoxy-carbonylbenzyl triphenylphosphonium bromide (1.52 g, 3 mmol) and potassium carbonate (0.41 g, 3 mmol) in dioxane (20 ml) was heated at reflux for 1 h. The solution was cooled to room temperature, followed by dropwise addition of 30% sodium methoxide solution in methanol (0.84 ml, 4.41 mmol). The mixture was heated at reflux for six hours. The reaction medium was concentrated on a rotary evaporator under vacuum at 40° C. 20 ml of water were added and the mixture was then acidified with concentrated hydrochloric acid solution to pH=1. This mixture was extracted with 30 ml of ethyl acetate. After separation of the phases once settling had taken place, the organic phase was washed twice with 20 ml of water, dried over anhydrous magnesium sulfate and concentrated on a rotary evaporator under vacuum at 40° C. The properties of the final product were as follows:

White solid. Mass: 710 mg. Yield: 60%. m.p.: 153° C.

$^1$H NMR (CDCl$_3$, 250 MHz): 1.48 (18H, s), 3.89 (3H, s), 5.23 (2H, s), 5.38 (1H, s), 6.68 (1H, s), 6.84 (1H, Ar, d, J=8 Hz), 7.25 (2H, Ar, s), 7.78 to 7.82 (2H, Ar, m).

$^{13}$C NMR (CDCl$_3$, 250 MHz): 30.24, 34.52, 51.92, 67.92, 115.25, 117.25, 121.86, 122.83, 123.34, 127.54, 128.28, 130.47, 133.15, 136.27, 154.40, 157.03, 166.86.

EXAMPLE 7

Synthesis of 3-[(3,5-di-tert-butyl-4-hydroxyphenyl)-2H-1-benzopyran]-6-carboxylic acid:

A solution of methyl 3-[(3,5-di-tert-butyl-4-hydroxyphenyl)-2H-1-benzopyran]-6-carboxylate (610 mg, 1.55 mmol), sodium hydroxide (260 mg, 6.2 mmol), lithium hydroxide (260 mg, 6.2 mmol), methanol (0.5 ml, and water (0.5 ml, in THF (5ml) was stirred for 4 days at room temperature. The solution was concentrated on a rotary evaporator under vacuum at 40° C. 10 ml of water and 10 ml of ethyl acetate were added and the mixture was then acidified to pH=1 with concentrated hydrochloric acid solution. The organic phase was washed twice with water, dried over anhydrous magnesium sulfate and concentrated on a rotary evaporator under vacuum at 40° C. The product was purified by flash chromatography on a column of silica (10% ethyl acetate, 90% CH$_2$Cl$_2$). Its properties were as follows:

White solid. Mass: 50 mg. Yield: 9%. m.p.: 244° C.

$^1$H NMR (CDCl$_3$, 250 MHz): 1.47 (18H, s), 5.33 (2H, s) 5.86 (1H, s), 6.69 (1H, s), 6.81 (1H, Ar, d, J=9 Hz), 7.46 (2H, Ar, s), 7.79 to 7.82 (2H, Ar, m).

$^{13}$C NMR (CDCl$_3$, 250 MHz): 14.57, 23.10, 30.66, 34.94, 68,42, 115.82, 122.28, 122.81, 123.045, 123.31, 127.87, 129.34, 131.69, 133.61, 136.71, 154.86, 158.23, 172.37.

EXAMPLE 8

Synthesis of methyl 3-[(4-(1-adamantyl)-3-methoxyphenyl)-2H-1-benzopyran]-6-carboxylate:

A mixture of 2 hydroxy-5-methoxy-carbonylbenzyl triphenylphosphonium bromide (1.4 g, 2.8 mmol), 4-(1-adamantyl)-3-methoxybromoacetophenone (0.9 g, 2.5 mmol) and potassium carbonate (0.35 g, 2.5 mmol) in dioxane was heated at reflux for 2 h. The mixture was cooled to room temperature followed by dropwise addition of 30% sodium methoxide solution in methanol (0.7 ml, 3.7 mmol). The mixture was heated for six hours at reflux. The reaction medium was concentrated on a rotary evaporator under vacuum at 40° C. 40 ml of water and 40 ml of ethyl acetate were added. The mixture was acidified with concentrated hydrochloric acid solution to pH=1. After separation of the phases once settling had taken place, the organic phase was washed twice with 40 ml of water, dried over anhydrous magnesium sulfate and concentrated on a rotary evaporator under vacuum at 40° C. The properties of the final product were as follows:

White solid. Mass: 337 mg. Yield: 32%. m.p.: 126° C.

$^1$H NMR (CDCl$_3$, 250 MHz): 1.77 (6H, s), 2.09 (9H, s), 3.89 (3H, s), 5.24 (2H, s), 6.79 (1H, s), 6.84 (1H, Ar, d, J=8.5 Hz), 6.93 to 6.96 (2H, m), 7.24 (1H, Ar, d, J=9 Hz), 7.79 to 7.84 (2H, m). $^{13}$C, NMR (CDCl$_3$, 250 Mhz): 29.20, 37.24, 40.68, 52.08, 55.20, 67.84, 108.13, 115.48, 117.19, 118.81, 122.58, 123.54, 127.05, 128.72, 131.04, 132.21, 134.90, 139.55, 157.38, 159.25, 166.89.

EXAMPLE 9

Synthesis of 3-[(4-(1-adamantyl)-3-methoxyphenyl)-2H-1-benzopyran]-6-carboxylic acid:

A solution of methyl 3-[(4-(1-adamantyl)-3-methoxyphenyl)-2H-1-benzopyran]-6-carboxylate (317 mg, 0.74 mmol), sodium hydroxide (60 mg, 1.5 mmol) and lithium hydroxide (60 mg, 1.5 mmol) in THF (5 ml) in the presence of water and methanol was stirred for 2 days at room temperature. The reaction medium was concentrated by distillation on a rotary evaporator under vacuum. 3 ml of water were added and the mixture was acidified to pH=1 with concentrated hydrochloric acid solution. After filtration, the solid obtained was washed with hexane and oven-dried. Its properties were as follows:

Light-yellow solid. Mass: 266 mg. Yield: 86%. m.p.: 250°–253° C.

$^1$H NMR (DMSO, 250 MHz): 1.70 (6H, s), 2.01 (9H, s), 3.81 (3H, s), 5.15 (2H, s), 6.72 (1H, s), 6.75 (1H, Ar, d, J=8.5 Hz), 6.85 to 6.87 (2H, m), 7.14 (1H, Ar, d, J=8.5 Hz), 7.74 to 7.78 (2H, Ar, m).

$^{13}$C NMR (DMSO, 250 MHz): 29.04, 37.01, 37.06, 40.50, 54.91, 67.59, 107.93, 115.13, 116.98, 118.75, 122.28, 124.04, 126.78, 128.86, 131.15, 131.88, 134.82, 139.17, 157.08, 159.05, 168.17.

EXAMPLE 10

Synthesis of methyl 3-[(3,5-di-tert-butyl-4-hydroxyphenyl)-2H-1-benzopyran]-7-carboxylate:

(a) Preparation of 3-(3,5-di-tert-butyl-4-hydroxyphenyl)-6-iodo-2H-1-benzopyran:

A suspension of 2-hydroxy-4-iodobenzyltriphenylphosphonium bromide (4 g, 6.9 mmol), potassium carbonate (1.64 g, 11.9 mmol) and 3,5-di-tert-butyl-4-hydroxybromoacetophenone in dioxane (80 ml) was heated at reflux for 1.5h. The solution was cooled to room temperature, followed by dropwise addition of a 30% solution of sodium methoxide in methanol (3.36 ml, 17.64 mmol). The mixture was heated for six hours at reflux. The reaction medium was concentrated on a rotary evaporator under vacuum at 40° C. 60 ml of water were added and the mixture was then acidified with concentrated hydrochloric acid solution to pH=1. This mixture was extracted with 60 ml of ethyl ether. After separation of the phases once settling had taken place, the organic phase was washed twice with 60 ml of water, dried over anhydrous magnesium sulfate and concentrated on a rotary evaporator under vacuum at 40° C. The product was purified by flash chromatography on a column of silica (30% CH$_2$Cl$_2$, 70% heptane). Its properties were as follows:

White solid. Mass: 2.2 g. Yield: 48w. m.p.: 153° C.

$^1$H NMR (CDCl$_3$, 250 MHz): 1.47 (18H, s), 5.13 (2H, s), 5.36 (1H, s), 6.60 (1H, s), 6.79 (1H, Ar, d, J=7.75 Hz), 7.20 to 7.24 (4H, Ar, m).

$^{13}$C NMR (CDCl$_3$, 250 MHz): 30.22, 34.47, 67.54, 91.82, 117.16, 121.81, 123.03, 124.39, 127.71, 130.60, 133.51, 136.20, 153.51, 154.29.

(b) Synthesis of methyl 3-[(3,5-di-tert-butyl-4-hydroxyphenyl)-2H-1-benzopyran]-7-carboxylate:

A solution of 3-(3,5-di-tert-butyl-4-hydroxyphenyl)-6-iodo-2H-1-benzopyran (2 g, 4.3 mmol), palladium diacetate (97 mg, 0.43 mmol) and tributylamine (2.06 ml, 8.6 mmol) in methanol (40 ml) was heated at 80° C. for 8h under a pressure of 2.5 bar of carbon monoxide. The reaction medium was concentrated on a rotary evaporator under vacuum at 40° C. 200 ml of ethyl acetate and water were added. The organic phase was washed twice with water (200 ml), dried over anhydrous magnesium sulfate and concentrated on a rotary evaporator under vacuum at 40° C. The product was purified by flash chromatography on a column of silica (70% CH$_2$Cl$_2$, 300 heptane). Its properties were as follows:

White solid. Mass: 2.2 g. Yield: 48%. m.p.: 153° C.

$^1$H NMR (DMSO, 250 MHz): 1.43 (18H, s), 3.84 (3H, s), 5.21 (2H, s), 6.88 (1H, s), 7.14 to 7.31 (4H, Ar, m), 7.51 (1H, Ar, d, J=8.5 Hz).

$^{13}$C NMR (CDCl$_3$, 250 MHz) : 30.16, 34.59, 51.89, 66.75, 115.24, 116.14, 121.45, 122.55, 126.48, 126.77, 127.76, 128.96, 135.64, 139.01, 152.23, 154.86, 165.67.

EXAMPLE 11

Synthesis of 3-[($^3$,$^5$-di-tert-butyl-4-hydroxyphenyl)-2H-1-benzopyran]-7-carboxylic acid:

A solution of methyl 3-[(3,5-di-tert-butyl-4-hydroxyphenyl)-2H-1-benzopyran]-7-carboxylate (900 mg, 2.28 mmol) and methane thiolate (660 mg, 9.4 mmol) in dimethylformamide (30 ml) was heated at 100° C. for 4 h. 20 ml of water and 20 ml of ethyl ether were added and the mixture was then acidified to pH=1 with concentrated hydrochloric acid solution. The organic phase was washed twice with water, dried over anhydrous magnesium sulfate and concentrated on a rotary evaporator under vacuum at 40° C. The product was purified by flash chromatography on a column of silica (40% ethyl acetate, 60% heptane). Its properties were as follows:

White solid. Mass: 775 mg. Yield: 89%. m.p.: 215° C.

$^1$H NMR (CDCl$_3$, 250 MHz) : 1.48 (18H, s) , 5.21 (2H, s) 5.41 (1H, s), 6.71 (1H, s), 7.15 (1H, Ar, d, J=8 Hz), 7.29 (2H, Ar, s), 7.56 (1H, Ar, s), 7.51 (1H, Ar, d, J=8Hz).

$^{13}$C NMR (CDCl$_3$, 250 MHz) : 29.80, 34.07, 67.09, 116.48, 116.74, 121.60, 123.38, 125.88, 127.00, 128.23, 128.39, 135.82, 135.88, 152.31, 154.24, 171.19.

EXAMPLE 12

Synthesis of methyl 3-[(3-(1-adamantyl)-4-hydroxyphenyl)-2H-1-benzopyran]-7-carboxylate:

(a) Preparation of 3-(1-adamantyl)-4-hydroxybromoacetophenone:

3-adamantyl-4-hydroxyacetophenone (2.5 g, 9.25 mmol) was dissolved in 15 ml of dioxane and 15 ml of ethyl ether. A solution of bromine (2.3 ml, 10.4 mmol) in dichloromethane (5 ml) was added dropwise. The mixture was stirred for one hour at room temperature. The reaction medium was poured into 100 ml of an ice-water mixture. After stirring and separation of the phases once settling had taken place, the organic phase was washed twice with 50 ml of water, dried over magnesium sulfate and concentrated on a rotary evaporator under vacuum at 40° C. The properties of the final product were as follows:

Pink solid. Mass: 1.8 g. Yield: 56%.

$^1$H NMR (CDCl$_3$, 250 MHz) : 1.78 (6H, s), 2.12 (9H, s), 4.40 (2H, s), 6.09 (1H, Ar, s), 6.75 (1H, Ar, d, J=8.25 Hz), 7.74 (1H, Ar, dd, J1=8.25 Hz, J2=2 Hz), 7.93 (1H, Ar, d, J=2Hz).

(b) Preparation of 2-hydroxy-4-iodobenzoic acid:

To 20% sulfuric acid solution (650 ml) were added 4-amino-2-hydroxybenzoic acid and 200 ml of 20% sulfuric acid solution. The solution was cooled to -10° C. and a solution of sodium nitrite (47 g, 0.34 mol) in water (100 ml) was added over 5 hours. The solution obtained was added dropwise to a suspension of potassium iodide (69.5 g, 0.42 mol) and copper(I) iodide (69.5 g, 0.36 mol) in 370 ml of 20% sulfuric acid. The mixture was stirred for 36 hours at room temperature and was then filtered. The filtrate was extracted with ethyl acetate, washed twice with saturated sodium sulfite solution and twice with water. The organic phase was concentrated on a rotary evaporator under vacuum at 40° C. The properties of the final product were as follows:

White solid. Mass: 24.25 g. Yield: 35%. m.p.: 192° C.

$^1$H NMR (DMSO, 250 MHz): 7.17 (1H, Ar, d, J=8.25 Hz), 7.25 (1H, Ar, s), 7.42 (1H, Ar, d, J=8.25 Hz).

(c) Preparation of 2-hydroxy-4-iodobenzyl alcohol:

A 1M solution of borane in THF was added dropwise at 0° C. to a solution of 2-hydroxy-4-iodobenzoic acid (13.2 g, 0.05 mol) in THF (100 ml). The mixture was stirred for 6 hours at room temperature and 20 ml of a solution of THF and water (1:1) were then added. After concentration on a rotary evaporator under vacuum at 40° C. The residue was extracted with ethyl acetate. The organic phase was washed with water, dried over anhydrous magnesium sulfate and concentrated on a rotary evaporator under vacuum at 40° C. The product was purified by flash chromatography on a column of silica (60% EtOAc, 40% heptane). Its properties were as follows:

White solid. Mass: 11 g. Yield: 88%.

$^1$H NMR (CDCl$_3$, 250 MHz) : 4.50 (2H, s), 6.81 (1H, Ar, d, J=7.75 Hz), 6.99 (1H, Ar, d, J=7.75 Hz), 7.05 (1H, Ar, s), 9.06 (1H, s).

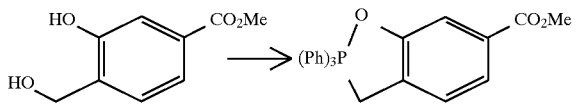

(d) Preparation of methyl 3-hydroxy-4-hydroxymethylbenzoate:

A solution of 2-hydroxy-4-iodobenzyl alcohol (1.25 g, 5 mmol), palladium diacetate (55 mg, 0.5 mmol) and triethylamine (1.4 ml, 10 mmol) in methanol (50 ml) was heated for 5 hours at 80° C. under carbon monoxide pressure (2.5 bar). After concentration on an evaporator under vacuum at 40° C., the oil obtained was diluted in dichloromethane (20 ml) and washed three times with 20 ml of water. The product was purified by flash chromatography on a column of silica (30% EtOAc, 30% CH$_2$Cl$_2$). Its properties were as follows: White solid. Mass: 640 mg. Yield: 70%.

$^1$H NMR (CDCl$_3$, 250 MHz) : 3.90 (3H, s), 4.90 (2H, s), 7.11 (1H, Ar, d, J=8 Hz), 7.51 (1H, Ar, d, J=8 Hz) 7.53 (1H, Ar, s).

(e) Preparation of 2-hydroxy-4-methyloxycarbonylbenzyltriphenylphosphonium bromide:

A suspension of triphenylphosphine hydrobromide (11.9 g, 34.7 mmol) and methyl 3-hydroxy-4-hydroxymethylbenzoate (6 g, 35 mmol) in acetonitrile (65 ml, was heated at reflux for 1.5 h. The solvent was removed on a rotary evaporator under vacuum and the resulting solid was diluted in ethyl ether (30 ml). The product was isolated by filtration. Its properties were as follows:

White solid. Mass: 16.3 mg. Yield: 91%.

$^1$H NMR (CDCl$_3$, 250 MHz): 3.70 (3H, s), 5.01 (2H, d, J=16.25 Hz), 7.01 (1H, Ar, d, J=8 Hz), 7.23 (1H, Ar, d, J=8 Hz) 7.40 (1H, Ar, s) 7.59 to 7.92 (15H, Ar, m).

(f) Preparation of 5-methoxycarbonyl-2,2,2-triphenyl-1,2 (3H)-benzoxaphosphole:

To a solution of $^2$-hydroxy-4-methoxycarbonyl-benzyltriphenylphosphonium bromide (2g, 3.94 mmol) in 44 ml of water were added 4.4 ml of 1N sodium hydroxide at room temperature. After stirring for 20 min, the precipitate was filtered off and dried. Its properties were as follows: Yellowish solid.

$^1$H NMR (CDCl$_3$, 250 MHz) : 3.77 (3H, s), 4.60 (2H, d, J=13.5 Hz), 6.90 (1H, Ar, d, J=7.75 Hz), 7.07 (1H, Ar, d, J=7.75 Hz), 7.34 (1H, Ar, s), 7.48 to 7.71 (15H, Ar, m).

(g) Synthesis of methyl 3-[(3-(1-adamantyl)-4-hydroxyophenyl)-2H-1-benzopyran]-7-carboxylate:

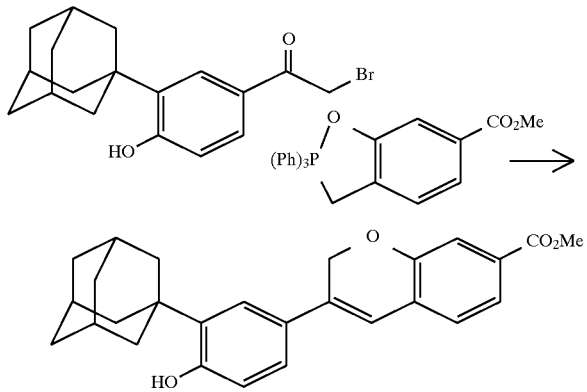

A solution of methyl 2,2,2-triphenyl-1,2(3H)-benzoxaphosphole-5-carboxylate (1.68 g, 3.94 mmol) and 3-(1-adamantyl)-4-hydroxybromoacetophenone (1.05 g, 3 mmol) in dichloromethane was stirred for 1 hour at room temperature. After concentration, 15 ml of dioxane are added. The solution was heated to reflux, followed by dropwise addition of a 300 solution of sodium methoxide in methanol (0.6 ml, 3.15 mmol). The heating was continued for 3 hours and the reaction medium was then concentrated on a rotary evaporator under vacuum at 40° C. 40 ml of water were added and the mixture was then extracted with 40 ml of ethyl ether. After separation of the phases once settling had taken place, the organic phase was washed twice with 40 ml of water, dried over anhydrous magnesium sulfate and concentrated on a rotary evaporator under vacuum at 40° C. The product was purified by crystallization from a dichloromethane/heptane mixture (2:8). Its properties were as follows:

Light-yellow solid. Mass: 520 mg. Yield: 41.5%. m.p.: 205° C.

$^1$H NMR (DMSO, 250 MHz): 1.74 (6H, s), 2.05 (3H, s), 2.11 (6H, s), 3.83 (3H, s), 5.20 (2H, s), 6.83 (1H, Ar, d, J=8.25 Hz), 6.94 (1H, s), 7.23 to 7.29 (4H, Ar, m), 7.51 (1H, Ar, d, J=8.25 Hz), 9.70 (1H, s).

$^{13}$C NMR (DMSO, 250 MHz): 28.32, 36.30, 36.54, 39.65, 51.96, 66.57, 115.06, 115.26, 116.49, 122.55, 123.15, 123.54, 125.79, 126.49, 127.87, 128.76, 135.14, 135.82, 152.14, 157.06, 165.68.

EXAMPLE 13

Synthesis of 3-[(3-(1-adamantyl)-4-hydroxvphenyl)-2H-1-benzopyran]-7-carboxylic acid:

A solution of methyl 3-[(3-(1-adamantyl)-4-hydroxyphenyl)-2H-1-benzopyran]-7-carboxylate (115 mg, 0.27 mmol), lithium hydroxide (50 mg, 1.25 mmol) and sodium hydroxide (50 mg, 1.25 mmol) in 5 ml of a mixture of THF, methanol and water (5/1/1) was heated at reflux for 4 hours. After concentration on a rotary evaporator under vacuum at 40° C., 5 ml of water and 5 ml of ethyl acetate were added. The mixture was acidified to pH 1 with concentrated hydrochloric acid solution. After separation of the phases once settling had taken place, the organic phase was washed twice with water, dried over anhydrous magnesium sulfate and concentrated on a rotary evaporator under vacuum at 40° C. The properties of the final product were as follows:

Light-yellow solid. Mass: 88 mg. Yield: 79%. m.p.: 293°–297° C.

¹H NMR (DMSO, 250 MHz): 1.58 (6H, s), 1.89 (3H, s), 1.95 (6H, s), 5.03 (2H, s), 6.66 (1H, Ar, d, J=8.25 Hz), 6.78 (1H, s), 7.08 to 7.11 (4H, Ar, m), 7.33 (1H, Ar, d, J=8.25 Hz), 9.53 (1H, s), 12.70 (1H, s).

¹³C NMR (DMSO, 250 MHz): 28.35, 36.35, 36.58, 39.70, 66.57, 115.32, 115.45, 116.54, 122.75, 123.16, 123.55, 125.93, 126.41, 127.51, 130.11, 134.88, 135.87, 152.12, 157.03, 166.80.

EXAMPLE 14

Synthesis of methyl 3-[(3-tert-butyl-4-hydroxyphenyl)-2H-1-benzopyran]-7-carboxylate:

A solution of methyl 2,2,2-triphenyl-1,2(3H)-benzoxaphosphole-5-carboxylate (203 mg, 0.75 mmol) and 3-tert-butyl-4-hydroxybromoacetophenone (305 mg, 0.72 mmol) in dichloromethane (3 ml) was stirred for 30 min at room temperature. After concentration, 3 ml of dioxane were added. The solution was heated at reflux, followed by dropwise addition of a 30% solution of sodium methoxide in methanol (0.15 ml, 0.78 mmol). The heating was continued for 3 hours and the reaction medium was then concentrated on a rotary evaporator under vacuum at 40° C. 10 ml of water were added and the mixture was extracted with 10 ml of ethyl ether. After separation of the phases once settling had taken place, the organic phase was washed twice with 10 ml of water, dried over anhydrous magnesium sulfate and concentrated on a rotary evaporator under vacuum at 40° C. The product was purified by flash chromatography on a column of silica (dichloromethane). Its properties were as follows:

White solid. Mass: 460 mg. Yield: 51%. m.p.: 159° C.

¹H NMR (CDCl₃, 250 MHz): 1.44 (9H, s), 3.90 (3H, s), 5.17 (2H, s), 5.25 (1H, s), 6.69 to 6.73 (2H, m), 7.10 (1H, Ar, d, J=7.75 Hz), 7.15 (1H, Ar, dd, J1=8.25 Hz, J2=2.25 Hz), 7.26 (1H, Ar, s), 7.39 (1H, Ar, d, J=1.75 Hz), 7.49 (1H, Ar, s), 7.60 (1H, Ar, d, J=7.75 Hz).

¹³C NMR (CDCl₃, 250 MHz) : 29.28, 34.56, 51.91, 67.18, 116.19, 116.69, 117.08, 122.93, 123.57, 123.83, 126.10, 127.51, 128.32, 129.60, 134.75, 136.41, 152.52, 154.75, 166.66.

EXAMPLE 15

Synthesis of 3-[(3-tert-butyl-4-hydroxyphenyl)-2H-1-benzopyran]-7-carboxylic acid:

A solution of methyl 3-[(3-tert-butyl-4-hydroxyphenyl)-2H-1-benzopyran]-7-carboxylate (100 mg, 0.3 mmol), lithium hydroxide (50 mg, 2 mmol) and sodium hydroxide (50 mg, 1.25 mmol) in 10 ml of a mixture of THF, methanol and water (5/1/1) was heated at reflux for 3 hours. After concentration on a rotary evaporator under vacuum at 40° C., 5 ml of water and 5 ml of ethyl acetate were added. The mixture was acidified to pH 1 with concentrated hydrochloric acid solution. After separation of the phases once settling had taken place, the organic phase was washed twice with water, dried over anhydrous magnesium sulfate and concentrated on a rotary evaporator under vacuum at 40° C. The properties of the final product were as follows:

White solid. Mass: 85 mg. Yield: 87%. m.p.: 208° C.

¯H NMR (CDCl₃, 250 MHz): 1.44 (9H, s), 3.90 (3H, s), 5.17 (2H, s), 6.71 (1H, s), 6.85 (1H, Ar, d, J=8.5 Hz), 7.08 to 7.15 (2H, Ar, m), 7.37 (1H, Ar, s), 7.49 (1H, Ar, s), 7.61 (1H, Ar, d, J=7.75 Hz) 8.61 (1H, s).

¹³C NMR (CDCl₃, 250 MHz): 29.20, 34.59, 67.17, 116.30, 116.57, 123.14, 123.38, 125.88, 126.75, 127.58, 130.01, 135.00, 136.30, 152.37, 156.51, 168.30.

¹H NMR (DMSO, 250 MHz): 1.43 (18H, s), 3.84 (3H, s), 5.21 (2H, s), 6.88 (1H, s), 7.14 to 7.31 (4H, Ar, m), 7.51 (1H, Ar, d, J=8.5 Hz).

EXAMPLE 16

Synthesis of methyl 3-[(3-(1-adamantyl)-4-methoxyethoxymethoxyphenyl)-2H-1-benzopyran]-7-carboxylate:

A solution of methyl 3-[(3-(1-adamantyl)-4-hydroxyphenyl)-2H-1-benzopyran]-7-carboxylate (165 mg, 0.4 mmol) and 80% sodium hydride (14 mg, 0.46 mmol) in DMF (2 ml) was stirred at 0° C. for 1 hour. Methoxyethoxymethyl chloride (0.054 ml, 0.47 mmol) was added dropwise at 0° C. The mixture was stirred for 12 hours at room temperature. 10 ml of water and 10 ml of ethyl acetate were added. The pH was adjusted to 1 with concentrated hydrochloric acid solution. The organic phase was washed twice with water, dried over anhydrous magnesium sulfate and concentrated on a rotary evaporator under vacuum at 40° C. The product was purified by flash chromatography on a column of silica (97% CH₂Cl₂, 3% ethyl ether, Rf: 0.52). Its properties were as follows:

Yellowish solid. Mass: 135 mg. Yield: 67%.

¹H NMR (CDCl₃, 250 MHz): 1.79 (6H, s), 2.13 (9H, s), 3.40 (3H, s), 3.59 (2H, t, J=4.5 Hz), 3.86 (2H, t, J=4.5 Hz), 3.90 (3H, s), 5.19 (2H, s), 5.35 (2H, s), 6.74 (1H, s), 7.11 (1H, Ar, d, J=7.75 Hz), 7.19 to 7.21 (2H, Ar, m), 7.37 (1H, Ar, s), 7.48 (1H, s), 7.59 (1H, Ar, d, J=7.75 Hz).

¹³C NMR (CDCl₃250 MHz) : 29.07, 37.07, 37.32, 40.67, 52.08, 59.09, 67.40, 67.97, 71.62, 93.33, 114.83, 116.41, 117.59, 123.11, 123.65, 126.35, 127.66, 129.31, 129.94, 134.98, 138.97, 152.79, 157.01, 166.74.

EXAMPLE 17

Synthesis of 3-[(3-(1-adamantyl)-4-methoxyethoxymethoxyphenyl)-2H-1-benzopyran]-7-carboxylic acid:

A solution of methyl 3-[(3-(1-adamantyl)-4-methoxyethoxymethoxyphenyl)-2H-1-benzopyran]-7-carboxylate (100 mg, 0.2 mmol), lithium hydroxide (50 mg, 1.25 mmol) and sodium hydroxide (50 mg, 1.25 mmol) in 5 ml of a mixture of THF, methanol and water (5/1/1) was heated at reflux for 5 hours. After concentration on a rotary evaporator under vacuum at 40° C., 5 ml of water and 5 ml of ethyl acetate were added. The mixture was acidified to pH 1 with concentrated hydrochloric acid solution. After separation of the phases once settling had taken place, the organic phase was washed twice with water, dried over anhydrous magnesium sulfate and concentrated on a rotary evaporator under vacuum at 40° C. The properties of the final product were as follows:

Light-yellow solid. Mass: 80 mg. Yield: 82%. m.p. 203°–204° C.

¹H NMR (DMSO, 250 MHz): 1.90 (6H, s), 2.14 (3H, s), 2.22 (6H, s), 3.39 (3H, S), 3.65 (2H, t, J=4.75 Hz), 3.93 (2H, t, J=4.75 Hz), 5.37 (2H, s), 5.49 (2H, s), 7.17 (1H, s), 7.25 (1H, Ar, d, J=9 Hz), 7.43 to 7.45 (2H, Ar, m), 7.50 to 7.53 (2H, Ar, m), 7.65 (1H, Ar, d, J=9 Hz), 13.01 (1H, s).

¹³C NMR (DMSO, 250 MHz): 28.49, 36.60, 36.83, 40.13, 58.16, 66.65, 67.97, 71.08, 93.02, 114.63, 115.52, 116.85, 122.88, 123.34, 123.92, 126.79, 127.39, 128.35, 130.58, 134.55, 138.14, 152.38, 156.48, 166.90.

EXAMPLES 18 AND 19

Synthesis of 3-[(5,6,7,8-tetrahydro-5,5,8,8-tetramethyl-2-naphthyl)-2H-1-benzopyran]-7-methyl alcohol and 3-[(5,6,7,8-tetrahydro-5,5,8,8-tetramethyl-2-naphthyl)-2H-1-benzopyran]-7-carboxaldehyde:

(a) Preparation of 5-iodo-2,2,2-triphenyl-1,2(3H)-benzoxaphosphole:

To a solution of 2-hydroxy-4-iodobenzyltriphenylphosphonium bromide (4g, 6.95 mmol) in 75 ml of water were added, at room temperature, 7.8 ml of 1N sodium hydroxide solution. After stirring for 30 min, the precipitate was filtered off and dried. Its properties were as follows: Yellowish solid.

(b) 7-iodo-3-(5,6,7,8-tetrahydro-5,5,8,8-tetramethyl-2-naphthyl)-2H-1-benzopyran:

A solution of 5-iodo-2,2,2-triphenyl-1,2(3H)-benzoxaphosphole (3.43 g, 6.95 mmol) and 5,6,7,8-tetrahydro-5,5,8,8-tetramethylbromoacetonaphthone (2.65 g, 8.6 mmol) in dichloromethane was stirred for 1 hour at room temperature. After concentration, 25 ml of dioxane were added. The solution was heated to reflux, followed by dropwise addition of a 30% solution of sodium methoxide in methanol (1.45 ml, 7.6 mmol). The heating is continued for 3 hours and the reaction medium was then concentrated on a rotary evaporator under vacuum at 40° C. 80 ml of water were added and the mixture was then extracted with 80 ml of ethyl ether. After separation of the phases once settling had taken place, the organic phase was washed twice with 80 ml of water, dried over anhydrous magnesium sulfate and concentrated on a rotary evaporator under vacuum at 40° C. The product was purified by flash chromatography (80% $CH_2Cl_2$, 20% hexane)(Rf: 0.37). Its properties were as follows:

Light-yellow solid. Mass: 2.03 g. Yield: 66%.
m.p.: 132° C.
$^1$H NMR ($CDCl_3$, 250 MHz) : 1.29 (6H, s), 1.31 (6H, s), 1.70 (4H, s), 5.14 (2H, s), 6.68 (1H, s), 6.79 (1H, Ar, d, J=7.75 Hz), 7.17 to 7.35 (5H, Ar, m).
$^{13}$C NMR (DMSO, 250 MHz): 32.19, 32.33, 34.73, 34.84, 35.37, 35.52, 67.85, 92.76, 118.82, 122.66, 123.23, 123.32, 124.95, 127.48, 128.37, 131.10, 133.25, 134.00, 145.81, 146.00, 154.15.

(c) Synthesis of 3-[(5,6,7,8-tetrahydro-5,5,8,8-tetramethyl-2-naphthyl)-2H-1-benzopyran]-7-methyl alcohol:

Synthesis of 3-[(5,6,7,8-tetrahydro-5,5,8,8-tetramethyl-2-naphthyl)-2H-1-benzopyran]-7-carboxaldehyde:

Synthesis of 3-[(5,6,7,8-tetrahydro-5,5,8,8-tetramethyl-2-naphthyl)-2H-1-benzopyran]-7-carboxylic acid:

A 2.5M solution of butyllithium in hexane (1 ml, 2.48 mmol) was added, at −70° C., to a solution of 7-iodo-3-(5,6,7,8-tetrahydro-5,5,8,8-tetramethyl-2-naphthyl)-2H-1-benzopyran (1 g, 2.25 mmol) in THF (10 ml). The mixture was stirred at −70° C. for 45 min. The temperature was permitted to warm to −45° C. and 0.2 ml of DMF (2.6 mmol) were added dropwise. The mixture was stirred at room temperature for 12 hours. 40 ml of ether and 40 ml of water were added and the mixture was stirred for 1 hour at room temperature. After separation of the phases once settling had taken place, the organic phase was washed twice with 40 ml of water. The acid and the alcohol were separated from the aldehyde by crystallization from dichloromethane. The acid was separated from the alcohol by crystallization from ethyl ether. The three products were washed with heptane.

The properties of the 3-[(5,6,7,8-tetrahydro-5,5,8,8-tetramethyl-2-naphthyl)-2H-1-benzopyran]-7-carboxaldehyde that was recovered were as follows:

Yellow solid. Mass: 42 mg. Yield: 5.4%. m.p.: 140° C.
$^1$H NMR ($CDCl_3$, 250 MHz) : 1.30 (6H, s), 1.32 (6H, s) , 1.71 (4H, s), 5.23 (2H, s), 6.79 (1H, s), 7.19 to 7.24 (2H, Ar, m), 7.32 to 7.44 (4H, Ar, m), 9.89 (1H, s).
$^{13}$C ($CDCl_3$ 250 MHz): 31.73, 31.88, 34.35, 34.41, 34.88, 35.03, 67.42, 100.78, 115.561, 118.31, 122.37, 123.09, 124.00, 127.06, 127.15, 129.09, 133.12, 136.00, 136.71, 145.51, 146.25, 153.53, 191.35.

The properties of the 3-[(5,6,7,8-tetrahydro-5,5,8,8-tetramethyl-2-naphthyl)-2H-1-benzopyran]-7-methyl alcohol that were recovered were as follows:

White solid. Mass: 118 g. Yield: 15%. m.p.: 126° C. $^1$H NMR ($CDCl_3$, 250 MHz) : 1.30 (6H, s) , 1.33 (6H, s) , 1.71 (4H, s), 4.64 (2H, s), 5.30 (2H, s), 6.76 (1H, s), 6.87 to 6.93 (2H, Ar, m), 7.09 (1H, Ar, d, J=7.5 Hz) 7.22 (1H, Ar, d, J=8.25 Hz), 7.33 to 7.38 (2H, Ar, m).
$^{13}$C ($CDCl_3$ 250 MHz): 31.49, 31.62, 33.99, 34.12, 34.69, 34.83, 64.94, 67.09, 113.72, 118.64, 119.76, 121.95, 122.36, 122.58, 126.68, 126.71, 131.94, 133.59, 141.65, 144.99 145.03, 153.20.

The properties of the 3-[(5,6,7,8-tetrahydro-5,5,8,8-tetramethyl-2-naphthyl)-2H-1-benzopyran]-7-carboxylic acid that was recovered were as follows:

White solid. Mass: 103 mg. Yield: 13%. m.p.: 285° C.
$^1$H NMR (DMSO, 250 MHz): 1.15 (6H, s), 1.2 (6H, s), 1.56 (4H, s), 5.15 (2H, s), 6.99 (1H, s), 7.24 (4H, Ar, m), 7.41 (2H, Ar, m,) , 12.78 (1H, s).
$^{13}$C (DMSO, 250 MHz): 31.64, 31.75, 34.15, 34.28, 34.65, 34.89, 66.76, 115.73, 117.98, 122.65, 123.02, 123.15, 127.06, 127.37, 130.96, 132.92, 134.77, 145.06, 145.47, 152.71, 167.01.

EXAMPLE 20

Synthesis of 3-[(3,5-di-tert-butyl-4-hydroxvphenyl)-2H-1-benzopyran]-7-carboxanilide:

A solution of 3-(3,5-di-tert-butyl-4-hydroxyphenyl)-6-iodo-2H-1-benzopyran (250 mg, 0.54 mmol) bis(triphenylphosphine)palladium(II) chloride (38 mg, 0.05 mmol) and aniline (94 μl, 1.1 mmol) in tributylamine (40 ml, was heated at 100° C. for 8 hours at a pressure of 2.5 bar of carbon monoxide. The reaction medium was treated with water and ethyl ether. The organic phase was washed with 2N hydrochloric acid solution and then with water, dried over anhydrous magnesium sulfate and concentrated on a rotary evaporator under vacuum at 40° C. The product was purified by flash chromatography on a column of silica ($CH_2Cl_2$) . Its properties were as follows:

White solid. Mass: 45 mg. Yield: 12%. m.p.: 50° C.
$^1$H NMR ($CDCl_3$, 250 MHz): 1.41 (18H, s), 5.13 (2H, s), 5.33 (1H, s), 6.63 (1H, s), 7.09 (2H, Ar, d, J=7.75 Hz), 7.21 to 7.36 (5H, Ar, m), 7.57 (2H, Ar, d, J=7.75 Hz), 7.75 (1H, Ar, s).
$^{13}$C NMR ($CDCl_3$, 250 MHz) : 30.61, 34.87, 67.97, 114.40, 117.41, 120.56, 120.80, 122.31, 124.80, 127.01, 127.16, 127.39, 127.84, 129.43, 132.90, 134.97, 135.63, 136.68, 138.42, 153.46, 154.94, 165.53.

EXAMPLES 21 AND 22

Synthesis of 3-[(5,6,7,8-tetrahydro-5,5,8,8-tetramethyl-2-naphthyl)-2H-1-benzopyran]-7-carboxylic acid morpholide and 3-[(5,6,7,8-tetrahydro-5,5,8,8-tetramethyl-2-naphthyl)-2H-1-benzopyran]-7-glyoxylic acid morpholide:

A solution of 7-iodo-3-(5,6,7,8-tetrahydro-5,5,8,8-tetramethyl-2-naphthyl)-2H-1-benzopyran (400 mg, 0.88 mmol) and bis(triphenylphosphine)-palladium (II) chloride (62 mg, 0.09 mmol) in morpholine (40 ml) was heated at 100° C. for 4 hours at a pressure of 2.5 bar of carbon monoxide. The reaction medium was treated with water and ethyl acetate. The organic phase was washed with 2N hydrochloric acid solution and then with water, dried over anhydrous magnesium sulfate and concentrated on a rotary evaporator under vacuum at 40° C. The products were separated by flash chromatography on a column of silica (EtOAc 4, heptane 6). The properties of the 3-[(5,6,7,8-tetrahydro-5,5,8,8-tetramethyl-2-naphthyl)-2H-1-benzopyran]-7-carboxylic acid morpholide that was recovered were as follows:

Yellow solid. Mass: 330 mg. Yield: 78%. m.p.: 162° C.

$^1$H NMR (CDCl$_3$, 250 MHz) : 1.22 (6H, s) , 1.25 (6H, s) , 1.63 (4H, s), 3.31 to 3.70 (8H, m), 5.21 (2H, s), 6.83 (1H, s), 6.93 (1H, Ar, d), 7.03 (1H, Ar, s), 7.23 to 7.38 (3H, Ar, m), 7.48 (1H, Ar, s).

The properties of the 3-[(5,6,7,8-tetrahydro-5,5,8,8-tetramethyl-2-naphthyl)-2H-1-benzopyran]-7-glyoxylic acid morpholide that were recovered were as follows:

Yellow solid. Mass: 50 mg. m.p.: 140° C.

$^1$H NMR (CDCl$_3$, 250 MHz) : 1.22 (6H, s) , 1.25 (6H, s) , 1.63 (4H, s), 3.31 (2H, t, J=5 Hz), 3.59 (2H, t, J=5 Hz), 3.71 (4H, s), 5.16 (2H, s), 6.79 (1H, s), 7.17 to 7.26 (3H, Ar, m), 7.30 to 7.31 (2H, Ar, m), 7.42 (1H, Ar, d, J1=1.5 Hz, J2=7.75 Hz).

EXAMPLE 23

Synthesis of N-butyl-3-[(5,6,7,8-tetrahydro-5,5,8,8-tetramethyl-2-naphthyl)-2H-1-benzopyran]-7-carboxamide:

The same procedure as in Examples 23 and 24 was carried out, but replacing the morpholine by N-butylamine. The properties of the final product were as follows:

Yellow solid. Mass: 33 mg.

$^1$H NMR (CDCl$_3$, 250 MHz) : 0.96 (3H, t) , 1.30 (6H, s), 1.32 (6H, s), 1.32 to 1.48 (2H, m), 1.54 to 1.66 (2H, m), 1.71 (4H, s), 3.39 (2H, 7), 5.13 (2H, s), 6.80 (1H, s), 7.03 to 7.58 (6H, m), 7.78 (1H, Ar, s), 8.00 (1H, Ar, d).

EXAMPLE 24

Biological activities:

| Compound of Example | F9 AC$_{50}$ (nM)$^a$ | RAR Transactivation AC$_{50}$ (nM)$^b$ | | | RAR binding Kd (nM)$^c$ | | |
|---|---|---|---|---|---|---|---|
| | | RARα | RARβ | RARγ | RARα | RARβ | RARγ |
| 1 | 34 | 8 | 2 | 4 | 764 | 71 | 174 |
| 13 | 107 | 47 | 20 | 6 | 821 | 3296 | 148 |
| 11 | 320 | 124 | 77 | 157 | 1471 | 3678 | 531 |
| 2 | 58 | 22 | 2 | 15 | 487 | 36 | 19 |

(a) After treatment with the compounds indicated, the mouse embryonic teratocarcinoma F9 cells differentiated into endodermal cells. This differentiation was characterized by the secretion of the plasminogen activator into the culture medium. The activity of the compound is expressed by the AC$_{50}$ value, which represents the concentration of test compound which produces half of the maximum amount of plasminogen activator secreted.

(b) This test was carried out as described in the publication: Bernard B. A., Bernardon J. M., Delescluse C., Martin C., Lenoir M. C., Maignan J., Carpentier B., Pilgrim W. R., Reichert U. and Shroot B., *Biochem. Biophys. Res. Comm.*, 186, 977–983 (1992). HeLa cells were cotransfected with expression vectors coding for human RARs and the reporter plasmid TREpp-tk-CAT. The value given represents the concentration of test compound which elicited 50% of the maximum CAT activity.

(c) The binding test was carried out on recombinant human receptors produced by the transfection of cos-7 cells with expression vectors coding for the RAR receptor subtypes. The nuclear extracts obtained from the transfected cells were used in experiments of competition with [H$^3$]-4-(5,6,7,8-tetrahydro-5,5,8,8-tetramethyl-2-anthracenyl benzoic acid (U.S. Pat. No. 5,196,577).

C. Examples of various specific formulations based on the compounds according to the invention:

EXAMPLE 25

(1) ORAL ROUTE:
   (a) The following composition was formulated as a 0.8 g tablet:
      (i) Compound of Example 2 0.005 g
      (ii) Pregelatinized starch 0.265 g
      (iii) Microcrystalline cellulose 0.300 g
      (iv) Lactose 0.200 g
      (v) Magnesium stearate 0.030 g For the treatment of acne, 1 to 3 tablets are administered to an adult individual per day for 3 to 6 months depending on the severity of the case treated.

(b) A drinkable suspension for packaging in 5 ml ampules was formulated:
      (i) Compound of Example 1 0.050 g
      (ii) Glycerol 0.500 g
      (iii) 700 Sorbitol 0.500 g
      (iv) Sodium saccharinate 0.010 g
      (v) Methyl para-hydroxybenzoate 0.040 g
      (vi) Flavoring, q.s.
      (vii) Purified water q.s 5 ml For the treatment of acne, 1 ampule is administered to an adult individual per day for 3 months depending on the severity of the case treated.

(c) The following formulation for packaging in gelatin capsules was formulated:
      (i) Compound of Example 3 0.025 g
      (ii) Corn starch 0.060 g
      (iii) Lactose q.s 0.300 g The capsules used were of gelatin, titanium dioxide and a preservative.

For the treatment of psoriasis, 1 capsule is administered to an adult individual per day for 30 days.

(2) TOPICAL ROUTE:
   (a) The following nonionic water-in-oil cream was formulated:
      (i) Compound of Example 3 0.100 g
      (ii) Mixture of emulsifying lanolin alcohols, waxes and refined oils, marketed by BDF under the tradename "anhydrous eucerin" 39.900 g
      (iii) Methyl para-hydroxybenzoate 0.075 g
      (iv) Propyl para-hydroxybenzoate 0.075 g
      (v) Sterile demineralized water q.s 100.000 g This cream is applied to psoriatic skin 1 to 2 times a day for 30 days.

(b) A gel was formulated from:
      (i) Compound of Example 1 0.050 g
      (ii) Erythromycin base 4.000 g
      (iii) Butylhydroxytoluene 0.050 g
      (iv) Hydroxypropylcellulose marketed by Hercules under the tradename "Klucel HF" 2.000 g
      (v) Ethanol (950 strength) q.s. 100.000 g This gel is applied to a skin affected with dermatosis or an acneic skin 1 to 3 times per day for 6 to 12 weeks depending on the severity of the case treated.

(c) An antiseborrhoea lotion was formulated by mixing together the following ingredients:
  (i) Compound of Example 1 0.030 g
  (ii) Propylene glycol 5.000 g
  (iii) Butylhydroxytoluene 0.100 g
  (iv) Ethanol (95° strength) q.s 100.000 g This lotion is applied twice a day to a seborrhoeic scalp and a significant improvement is observed within a period of 2 to 6 weeks.

(d) A cosmetic composition to counter the deleterious effects of the sun was formulated by mixing together the following ingredients:
  (i) Compound of Example 5 1.000 g
  (ii) Benzylidenecamphor 4.000 g
  (iii) Fatty acid triglycerides 31.000 g
  (iv) Glyceryl monostearate 6.000 g
  (v) Stearic acid 2.000 g
  (vi) Cetyl alcohol 1.200 g
  (vii) Lanolin 4.000 g
  (viii) Preservatives 0.300 g
  (ix) Propylene glycol 2.000 g
  (x) Triethanolamine 0.500 g
  (xi) Fragrance 0.400 g
  (xii) Demineralized water q.s 100.000 g This composition is applied daily and combats photoinduced aging.

(e) The following nonionic oil-in-water cream was formulated:
  (i) Compound of Example 1 0.500 g
  (ii) Vitamin D3 0.020 g
  (iii) Cetyl alcohol 4.000 g
  (iv) Glyceryl monostearate 2.500 g
  (v) PEG 50 stearate 2.500 g
  (vi) Karite butter 9.200 g
  (vii) Propylene glycol 2.000 g
  (viii) Methyl para-hydroxybenzoate 0.075 g
  (ix) Propyl para-hydroxybenzoate 0.075 g
  (x) Sterile demineralized water q.s 100.000 g This cream is applied to a psoriatic skin 1 to 2 times a day for 30 days.

(f) A topical gel was formulated by mixing together the following ingredients:
  (i) Compound of Example 2 0.050 g
  (ii) Ethanol 43.000 g
  (iii) α-Tocopherol 0.050 g
  (iv) Carboxyvinyl polymer marketed under the trademark "Carbopol 941" by Goodrich 0.500 g
  (v) Triethanolamine as a 20% aqueous solution by weight 3.800 g
  (vi) Water 9.300 g
  (vii) Propylene glycol q.s. 100.000 g This gel is applied in the treatment of acne 1 to 3 times a day for 6 to 12 weeks depending on the severity of the case treated.

(g) A lotion for combating hair loss and for the regrowth of the hair was formulated by mixing together the following ingredients:
  (i) Compound of Example 3 0.05 g
  (ii) Compound marketed under the trademark "Minoxidil" 1.00 g
  (iii) Propylene glycol 20.00 g
  (iv) Ethanol 34.92 g
  (v) Polyethylene glycol (molecular weight=400) 40.00 g
  (vi) Butylhydroxyanisole 0.01 g
  (vii) Butylhydroxytoluene 0.02 g
  (viii) Water q.s. 100.000 g This lotion is applied twice a day for 3 months to a scalp which has suffered considerable hair loss.

(h) An antiacne cream was formulated by mixing together the following ingredients:
  (i) Compound of Example 1 0.050 g
  (ii) Retinoic acid 0.010 g
  (iii) Mixture of stearates of glycerol and of polyethylene glycol (75 mol) marketed under the trademark "Gelot 64" by Gattefosse 15.000 g
  (iv) Palm Kernel oil polyoxyethylenated with 6 mol of ethylene oxide, marketed under the trademark "Labrafil M2130 CS" by Gattefosse 8.000 g
  (v) Perhydrosqualene 10.000 g
  (vi) Preservatives qs
  (vii) Polyethylene glycol (molecular weight=400) 8.000 g
  (viii) Disodium salt of ethylenediaminetetraacetic acid 0.050 g
  (ix) Purified water q.s. 100.000 g This cream is applied to a skin affected with dermatosis or an acneic skin 1 to 3 times a day for 6 to 12 weeks.

(i) An oil-in-water cream was formulated from the following constituents:
  (i) Compound of Example 2 0.020 g
  (ii) Betamethasone 17-valerate 0.050 g
  (iii) S-Carboxymethylcysteine 3.000 g
  (iv) Polyoxyethylene stearate (40 mol of ethylene oxide) marketed under the trademark "Myrj 52" by Atlas 4.000 g
  (v) Sorbitan monolaurate polyoxyethylenated with 20 mol of ethylene oxide, marketed under the trademark "Tween 20" by Atlas 1.800 g
  (vi) Mixture of glyceryl mono- and distearate marketed under the trademark "Geleol" by Gattefosse 4.200 g
  (vii) Propylene glycol 10.000 g
  (viii) Butylhydroxyanisole 0.010 g
  (ix) Butylhydroxytoluene 0.020 g
  (x) Cetostearyl alcohol 6.200 g
  (xi) Preservatives q.s.
  (xii) Perhydrosqualene 18.000 g
  (xiii) Mixture of caprylic/capric triglycerides marketed under the trademark "Miglyol 812" by Dynamit Nobel 4.000 g
  (xiv) Triethanolamine (99% by weight) 2.500 g
  (xv) Water q.s. 100.000 g This cream is applied twice a day to a skin affected by dermatosis, for 30 days.

(j) The following oil-in-water type cream was formulated:
  (i) Lactic acid 5.000 g
  (ii) Compound of Example 2 0.020 g
  (iii) Polyoxyethylene stearate (40 mol of ethylene oxide) marketed under the trademark "Myrj 52" by Atlas 4.000 g
  (iv) Sorbitan monolaurate polyoxyethylenated with 20 mol of ethylene oxide, marketed under the trademark "Tween 20" by Atlas 1.800 g
  (v) Mixture of glyceryl mono- and distearate marketed under the trademark "Geleol" by Gattefosse 4.200 g
  (vi) Propylene glycol 10.000 g
  (vii) Butylhydroxyanisole 0.010 g
  (viii) Butylhydroxytoluene 0.020 g
  (ix) Cetostearyl alcohol 6.200 g
  (x) Preservatives q.s.
  (xi) Perhydrosqualene 18.000 g
  (xii) Mixture of caprylic/capric triglycerides marketed under the trademark "Miglyol 812" by Dynamit Nobel 4.000 g
  (xiii) Water q.s. 100.000 g This cream is applied once a day and is useful in combating aging, whether photoinduced or chronological.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polyaromatic heterocyclic compound having the structural formula (I):

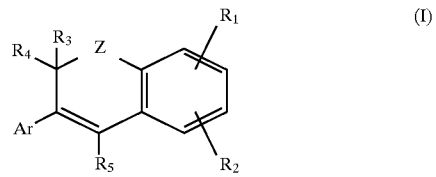

in which Z is —O—; Ar is either a radical having the following structural formula (II):

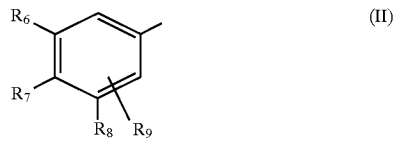

or a radical having the following structural formula (III):

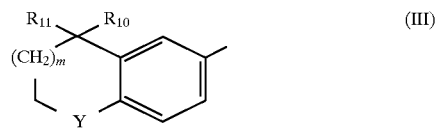

wherein m is equal to 0 or 1; $R_1$ is (i) a hydrogen atom, (ii) the —$CH_3$ radical, (iii) a radical —$(CH_2)_p$—O—$R_{12}$, (iv) a radical $OR_{12}$, (v) a radical:

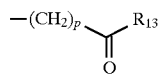

or (vi) a radical —$S(O)_tR_{14}$, wherein $R_{12}$, $R_{13}$, $R_{14}$, p and t are as defined below; $R_2$ is a hydrogen atom, a halogen atom, a lower alkyl radical or a radical —$OR_{12}$I wherein $R_{12}$ is as defined below; $R_3$ and $R_4$, which may be identical or different, are each a halogen atom, a hydrogen atom, a lower alkyl radical or a radical $OR_{12}$, wherein $R_{12}$ is as defined below; $R_5$ is a halogen atom, a hydrogen atom, a lower alkyl radical or a radical —$OR_{15}$, wherein $R_{15}$ is as defined below; $R_6$, $R_7$, $R_8$ and $R_9$, which may be identical or different, are each a hydrogen atom, a halogen atom, an alkyl radical, a cycloalkyl radical, a radical —$(Z_2)_n$—$(CH_2)_q$—CO—$R_{13}$ or a radical —$Z_2$—$R_{12}$, with the proviso that at least two of the radicals $R_6$, $R_7$, $R_8$ and $R_9$ are other than a hydrogen atom and further wherein $Z_1$, $Z_2$, $R_{12}$, $R_{13}$, n and q are as defined below; $R_{10}$ and $R_{11}$ are lower alkyl radicals; Y is a divalent radical selected from among —C($R_{11}$)$_2$—, —O—, —S—, —CH(OH)—, —CO—, —SO— and —$SO_2$—, wherein $R_{11}$ is as defined above, with the proviso that $R_1$, $R_2$, $R_3$, $R_4$ and $R_5$ cannot simultaneously each be a hydrogen atom; $R_{12}$ is a hydrogen atom, a lower alkyl radical, an aryl radical, an aralkyl radical, a polyhydroxyalkyl radical, a polyether radical or a lower acyl radical; $R_{13}$ is (a) a hydrogen atom, (b) a radical:

wherein r and r' are as defined below, or (c) a radical —$OR_{14}$, wherein $R_{14}$ is as defined below; $R_{14}$ is a hydrogen atom, an alkyl radical, a mono- or polyhydroxyalkyl radical, an optionally substituted aryl or aralkyl radical, or a sugar or amino acid residue; $R_1$ is a hydrogen atom, a lower alkyl radical, an aryl radical, an aralkyl radical or a polyether radical; r and r', which may be identical or different, are each a hydrogen atom, a lower alkyl radical, an optionally substituted aryl radical, or an amino acid or sugar residue, or r and r' may together form, with the nitrogen atom from which they depend, a heterocycle; $Z_1$ is O, S or Nr'; $Z_2$ is O, n is equal to 0 or 1; p is equal to 0, 1, 2 or 3; q is an integer ranging from 0 to 10; t is equal to 0, 1, 2 or 3; and the further provisos that at least one of $R_6$, $R_7$, $R_8$ and $R_9$ is a cycloalkyl radical or an alkyl radical selected from the group consisting of isopropyl and tert-butyl radicals; and $R_1$ and $R_2$ cannot be —O—$R_{12}$ or $(CH_2)_pOR_{12}$, when p equals 0. Ar is of formula (II), and one of the substituents $R_6$, $R_7$, $R_8$ or $R_9$ is an alkyl radical; and the pharmaceutically/cosmetically acceptable optical and geometric isomers and salts thereof.

2. A polyaromatic heterocyclic compound as defined by claim 1, wherein formula (I), Ar has the structural formula (III).

3. A polyaromatic heterocyclic compound as defined by claim 1, comprising a pharmaceutically acceptable salt thereof.

4. A polyaromatic heterocyclic compound as defined by claim 1, wherein formula (I), the lower alkyl radical substituents are selected from among methyl, ethyl, isopropyl, butyl, tert-butyl and hexyl radicals.

5. A polyaromatic heterocyclic compound as defined by claim 1, wherein formula (I), the lower acyl radical substituents are selected from among acetyl, propionyl or pivaloyl radicals.

6. A polyaromatic heterocyclic compound as defined by claim 1, wherein formula (I), the monohydroxyalkyl radical substituents are selected from among 2-hydroxyethyl, 2-hydroxypropyl and 3-hydroxypropyl radicals.

7. A polyaromatic heterocyclic compound as defined by claim 1, wherein formula (I), the polyhydroxyalkyl radical substituents are selected from among 2,3-dihydroxypropyl, 2,3,4-trihydroxybutyl, 2,3,4,5-tetrahydroxypentyl and pentaerythritol radicals.

8. A polyaromatic heterocyclic compound as defined by claim 1, wherein formula (I), the aryl radical substituents are selected from among phenyl radicals optionally substituted by at least one halogen atom, or at least one hydroxyl or nitro functional group.

9. A polyaromatic heterocyclic compound as defined by claim 1, wherein formula (I), the aralkyl radical substituents are selected from among benzyl and phenethyl radicals optionally substituted by at least one halogen atom, or at least one hydroxyl or nitro functional group.

10. A polyaromatic heterocyclic compound as defined by claim 1, wherein formula (I), the cycloalkyl radical substituents have from 1 to 10 carbon atoms and are optionally substituted by at least one halogen atom, or at least one hydroxyl functional group, or at least one adamantyl or 1-methylcyclohexyl radical.

11. A polyaromatic heterocyclic compound as defined by claim 1, wherein formula (I), the sugar residue substituents are selected from among those of glucose, galactose, mannose and glucuronic acid.

12. A polyaromatic heterocyclic compound as defined by claim 1, wherein formula (I), the amino acid residue substituents are selected from among those of lysine, glycine and aspartic acid.

13. A polyaromatic heterocyclic compound as defined by claim 1, wherein formula (I), the heterocyclic radical substituents are selected from among piperidino, morpholino, pyrrolidino and piperazino radicals which are optionally substituted by a $C_1$–$C_6$ alkyl radical or a mono- or polyhydroxyalkyl radical.

14. A polyaromatic heterocyclic compound as defined by claim 1, wherein formula (I), the halogen atom substituents are selected from among fluorine, chlorine and bromine atoms.

15. A polyaromatic heterocyclic compound as defined by claim 1, wherein formula (I), at least one of the following conditions is satisfied:

$R_1$ is a radical —$(CH_2)_p$—CO—O—$R_{14}$;

$R_2$, $R_3$, $R_4$, $R_5$, $R_6$ and $R_9$ are hydrogen atoms;

$R_7$ is a cycloalkyl radical;

$R_8$ is a radical —$OR_{12}$;

Y is a radical $C(R_{11})_2$.

16. A polyaromatic heterocyclic compound as defined by claim 1, selected from among 3-[(3-(1-adamantyl)-4-methoxyphenyl)-2H-1-benzopyran]-7-carboxylic acid; methyl 3-[(3-(1-adamantyl)-4-methoxyphenyl)-2H-1-benzopyran]-7-carboxylate; methyl 3-[(3-(1-adamantyl)-4-hydroxyphenyl)-2H-1-benzopyran]-7-carboxylate; 3-[(3-(1-adamantyl)-4-hydroxyphenyl)-2H-1-benzopyran]-7-carboxylic acid; 3-[(3-(1-adamantyl)-4-methoxyphenyl)-2H-1-benzopyran]-6-carboxylic acid; methyl 3-[(3-(1-adamantyl)-4-methoxyphenyl)-2H-1-benzopyran]-6-carboxylate; 3-[(3-(1-adamantyl)-4-hydroxyphenyl)-2H-1-benzopyran]-6-carboxylic acid; 3-(5,6,7,8-tetrahydro-5,5,8,8-tetramethyl-2-naphthyl)-2H-1-benzopyran]-7-carboxylic acid; methyl 3-[(5,6,7,8-tetrahydro-5,5,8,8-tetramethyl-2-naphthyl)-2H-1-benzopyran]-7-carboxylate; 3-[(5,6,7,8-tetrahydro-5,5,8,8-tetramethyl-2-naphthyl)-2H-1-benzopyran]-6-carboxylic acid; methyl 3-[(5,6,7,8-tetrahydro-5,5,8,8-tetramethyl-2-naphthyl)-2H-1-benzopyran]-6-carboxylate; methyl 3-[(3,5-di-tert-butyl-4-hydroxyphenyl)-2H-1-benzopyran]-6-carboxylate; 3-[(3,5-di-tert-butyl-4-methoxyphenyl)-2H-1-benzopyran]-6-carboxylic acid; 3-[(3,5-di-tert-butyl-4-hydroxyphenyl)-2H-1-benzopyran]-6-carboxylic acid; methyl 3-[(3,5-di-tert-butyl-4-methoxyphenyl)-2H-1-benzopyran]-7-carboxylate; methyl 3-[(3,5-di-tert-butyl-4-methoxyphenyl)-2H-1-benzopyran]-6-carboxylate; 3-[(3,5-di-tert-butyl-4-hydroxyphenyl)-2H-1-benzopyran]-7-carboxylic acid; 3-[(3,5-di-tert-butyl-4-methoxyphenyl)-2H-1-benzopyran]-7-carboxylic acid; methyl 3-[(4-(1-adamantyl)-3-methoxyphenyl)-2H-1-benzopyran]-6-carboxylate; 3-[(4-(1-adamantyl)-3-methoxyphenyl)-2H-1-benzopyran]-6-carboxylic acid; methyl 3-[(3-tert-butyl-4-hydroxyphenyl)-2H-1-benzopyran]-7-carboxylate; 3-[(3-tert-butyl-4-hydroxyphenyl)-2H-1-benzopyran]-7-carboxylic acid; methyl 3-[(3-(1-adamantyl)-4-methoxyethoxymethoxyphenyl)-2H-1-benzopyran]-7-carboxylate; 3-[(3-(1-adamantyl)-4-methoxyethoxymethoxyphenyl)-2H-1-benzopyran]-7-carboxylic acid; 3-[(5,6,7,8-tetrahydro-5,5,8,8-tetramethyl-2-naphthyl)-2H-1-benzopyran]-7-methyl alcohol; 3-[(5,6,7,8-tetrahydro-5,5,8,8-tetramethyl-2-naphthyl)-2H-1-benzopyran]-7-carboxaldehyde; 3-[(3,5-di-tert-butyl-4-hydroxyphenyl)-2H-1-benzopyran]-7-carboxanilide; 3-[(5,6,7,8-tetrahydro-5,5,8,8-tetramethyl-2-naphthyl)-2H-1-benzopyran]-7-carboxylic acid morpholide; 3-[(5,6,7,8-tetrahydro-5,5,8,8-tetramethyl-2-naphthyl)-2H-1-benzopyran]-7-glyoxylic acid morpholide; N-butyl-3-[(5,6,7,8-tetrahydro-5,5,8,8-tetramethyl-2-naphthyl)-2H-1-benzopyran]-7-carboxamide; and methyl 3-[(3,5-di-tert-butyl-4-hydroxyphenyl)-2H-1-benzopyran]-7-carboxylate.

17. A pharmaceutical composition of matter, comprising a therapeutically effective amount of a polyaromatic heterocyclic compound as defined by claim 1, or pharmaceutically acceptable salt or isomer thereof, and a pharmaceutically acceptable carrier, diluent or vehicle therefor.

18. The pharmaceutical composition as defined by claim 17, further comprising a retinoid compound, a D vitamin or derivative thereof, a corticosteroid or estrogen, an anti-free radical agent, an antioxidant, an α-hydroxy or α-keto acid or derivative thereof, an ion channel blocker, or combination thereof.

19. The pharmaceutical composition as defined by claim 17, comprising a tablet, a capsule, a syrup, a suspension, an elixir, a solution, a powder, granules, an emulsion, microspheres, nanospheres, lipid vesicles, polymeric vesicles, or an injectable.

20. The pharmaceutical composition as defined by claim 17, comprising an ointment, a cream, a milk, a pommade, a salve, an impregnated pad, a gel, a spray, or a lotion.

21. The pharmaceutical composition as defined by claim 17, adopted for topical administration.

22. The pharmaceutical composition as defined by claim 17, adopted for systemic administration.

23. The pharmaceutical composition as defined by claim 17, comprising from 0.001% to 5% by weight of said polyaromatic heterocyclic compound, or salt or isomer thereof.

24. A method for treating a dermatological disorder in a mammalian organism in need of such treatment, comprising administering to such organism a therapeutically effective amount of the pharmaceutical composition as defined by claim 17.

25. A method for treating skin aging in a mammalian organism in need of such treatment, comprising administering to such organism a therapeutically effective amount of the pharmaceutical composition as defined by claim 17.

26. A method for treating epidermal and/or dermal atrophy in a mammalian organism in need of such treatment, comprising administering to such organism a therapeutically effective amount of the pharmaceutical composition as defined by claim 17.

27. A method for treating a cicatrization disorder in a mammalian organism in need of such treatment, comprising administering to such organism a therapeutically effective amount of the pharmaceutical composition as defined by claim 17.

28. A method for treating a sebaceous function disorder in a mammalian organism in need of such treatment, comprising administering to such organism a therapeutically effective amount of the pharmaceutical composition as defined by claim 17.

29. A cosmetic composition of matter, comprising a cosmetically effective amount of a polyaromatic heterocyclic compound as defined by claim 1, or cosmetically acceptable salt or isomer thereof, and a cosmetically acceptable carrier, diluent or vehicle therefor.

30. The cosmetic composition as defined by claim 29, comprising a cream, a milk, a lotion, a gel, microspheres, nanospheres, lipid vesicles, polymeric vesicles, a soap, or a shampoo.

31. The cosmetic composition as defined by claim 29, comprising from 0.001% to 3% by weight of said polyaromatic heterocyclic compound, or salt or isomer thereof.

32. The cosmetic composition as defined by claim 29, further comprising a retinoid compound, a D vitamin or derivative thereof, a corticosteroid or estrogen, an anti-free radical agent, an antioxidant, an α-hydroxy or α-keto acid or derivative thereof, an ion channel blocker, or combination thereof.

33. A method for treating a skin or hair disorder on a mammalian organism in need of such treatment, comprising administering to such organism a cosmetically/therapeutically effective amount of the cosmetic composition as defined by claim 29.

34. The pharmaceutical composition as defined by claim 17, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

35. The pharmaceutical composition as defined by claim 17, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

36. The cosmetic composition by claim 29, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

37. The cosmetic composition as defined by claim 29, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *

UNITED STATES PATENT AND TRADEMARK OFFICE
CERTIFICATE OF CORRECTION

PATENT NO. : 5,849,798
DATED : December 15, 1998
INVENTOR(S) : Bruno Charpentier et al.

It is certified that error appears in the above-indentified patent and that said Letters Patent is hereby corrected as shown below:

Please replace Sheet 2 of 2, Fig. 2, with the attached Fig. 2.

Column 2, line 46, please change "g" to --q--.

Column 4, line 54, please change "$^3$-[" to --3-[--.

Column 8, line 33, please change "0.00%" to --0.001%--.

Column 12, line 3, please change "$^3$-[" to --3-[--.

Column 12, line 27, please change "$^3$-[" to --3-[--.

Column 18, line 14, please change "3-[($^3$,$^5$-di-tert-butyl-4-hydroxyphenyl)-" to --3-[(3,5-di-tert-butyl-4-hydroxyphenyl)- --.

Signed and Sealed this

Twenty-eighth Day of September, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,849,798
DATED : December 15, 1998
INVENTOR(S) : Bruno Charpentier et al.

It is certified that error appears in the above-indentified patent and that said Letters Patent is hereby corrected as shown below:

Column 29, line 55, please change "$Z_2$" to --$Z_1$--.

Column 30, line 10, please change "$R_1$" to --$R_{15}$--.